(12) United States Patent
Hauptmann et al.

(10) Patent No.: US 9,592,105 B2
(45) Date of Patent: *Mar. 14, 2017

(54) DENTAL BLANK COMPRISING A PRE-SINTERED POROUS ZIRCONIA MATERIAL, PROCESS OF ITS PRODUCTION AND DENTAL ARTICLE FORMED FROM SAID DENTAL BLANK

(71) Applicant: 3M INNOVATIVE PROPERTIES COMPANY, Saint Paul, MN (US)

(72) Inventors: Holger Hauptmann, Sindelsdorf (DE); Sybille Schmittner, Buch (DE); Gallus Schechner, Herrsching (DE); Brant U. Kolb, Afton, MN (US); Andreas Herrmann, München (DE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/418,973

(22) PCT Filed: Aug. 1, 2013

(86) PCT No.: PCT/US2013/053181
§ 371 (c)(1),
(2) Date: Feb. 2, 2015

(87) PCT Pub. No.: WO2014/022643
PCT Pub. Date: Feb. 6, 2014

(65) Prior Publication Data
US 2015/0238291 A1    Aug. 27, 2015

(30) Foreign Application Priority Data
Aug. 3, 2012    (EP) .................................... 12179125

(51) Int. Cl.
*A61C 13/00*    (2006.01)
*C04B 35/486*    (2006.01)
(Continued)

(52) U.S. Cl.
CPC ............ *A61C 13/0022* (2013.01); *A61C 5/10* (2013.01); *A61C 7/00* (2013.01); *A61C 8/0001* (2013.01);
(Continued)

(58) Field of Classification Search
None
See application file for complete search history.

(56) References Cited

U.S. PATENT DOCUMENTS 6,228,340 B1 * 5/2001  Imhof ..................... C01B 37/02
                                                                501/103
6,713,421 B1 * 3/2004  Hauptmann .......... C04B 35/486
                                                                433/202.1
(Continued)

FOREIGN PATENT DOCUMENTS

DE     WO 2013055432 A1 *  4/2013  .......... C04B 35/486
WO     WO 03/032861         4/2003
(Continued)

OTHER PUBLICATIONS

Quinelato et al. 2000. *Journal of the European Ceramic Society.* 20(8):1077-84. "Effect of ceria content on the sintering of Zr02 based ceramics synthesized from a polymeric precursor."
(Continued)

*Primary Examiner* — David Sample
*Assistant Examiner* — Nicholas W Jordan

(57) ABSTRACT

The invention relates to a dental mill blank comprising a pre-sintered porous zirconia material, the porous pre-sintered zirconia material showing a N2 adsorption of isotherm type IV according to IUPAC classification, the porous pre-
(Continued)

sintered zirconia material having a Vickers hardness from about 25 to about 150, the dental mill blank comprising means for reversible attaching it to a machining device. The invention also relates to a process of producing a zirconia dental article comprising the steps of providing a dental mill blank comprising a porous pre-sintered zirconia material, placing the dental mill blank in a machining device, machining the porous zirconia material and to a dental article obtained by such a process.

15 Claims, 2 Drawing Sheets

(51) Int. Cl.
| | |
|---|---|
| C04B 35/626 | (2006.01) |
| C04B 35/632 | (2006.01) |
| C04B 35/634 | (2006.01) |
| C04B 35/638 | (2006.01) |
| C04B 38/00 | (2006.01) |
| B82Y 30/00 | (2011.01) |
| A61C 5/10 | (2006.01) |
| A61C 7/00 | (2006.01) |
| A61C 8/00 | (2006.01) |
| A61C 13/01 | (2006.01) |
| A61C 13/08 | (2006.01) |
| C04B 35/48 | (2006.01) |
| C04B 111/00 | (2006.01) |

(52) U.S. Cl.
CPC .......... *A61C 8/005* (2013.01); *A61C 13/0006* (2013.01); *A61C 13/01* (2013.01); *A61C 13/08* (2013.01); *B82Y 30/00* (2013.01); *C04B 35/48* (2013.01); *C04B 35/486* (2013.01); *C04B 35/6263* (2013.01); *C04B 35/6269* (2013.01); *C04B 35/632* (2013.01); *C04B 35/638* (2013.01); *C04B 35/63424* (2013.01); *C04B 35/63488* (2013.01); *C04B 38/0045* (2013.01); *C04B 2111/00836* (2013.01); *C04B 2235/3217* (2013.01); *C04B 2235/3225* (2013.01); *C04B 2235/3227* (2013.01); *C04B 2235/3248* (2013.01); *C04B 2235/449* (2013.01); *C04B 2235/5409* (2013.01); *C04B 2235/5454* (2013.01); *C04B 2235/6023* (2013.01); *C04B 2235/612* (2013.01); *C04B 2235/6562* (2013.01); *C04B 2235/6565* (2013.01); *C04B 2235/6567* (2013.01); *C04B 2235/781* (2013.01); *C04B 2235/945* (2013.01); *C04B 2235/95* (2013.01); *C04B 2235/96* (2013.01); *F04C 2270/041* (2013.01); *Y10T 428/21* (2015.01); *Y10T 428/2457* (2015.01); *Y10T 428/24479* (2015.01)

(56) References Cited

U.S. PATENT DOCUMENTS

| | | | |
|---|---|---|---|
| 7,101,819 B2 | 9/2006 | Rosenflanz | |
| 2006/0292527 A1* | 12/2006 | Basler | A61C 13/0022 433/213 |
| 2007/0108645 A1 | 5/2007 | Van Schroeter | |
| 2008/0303181 A1* | 12/2008 | Holand | A61O 5/10 501/103 |
| 2010/0041542 A1* | 2/2010 | Rolf | A61C 8/0012 501/104 |
| 2013/0277873 A1* | 10/2013 | Sadoun | A61O 5/10 264/16 |
| 2015/0223917 A1* | 8/2015 | Herrmann | A61K 6/0005 433/203.1 |
| 2015/0282905 A1* | 10/2015 | Jahns | A61K 6/0245 428/312.8 |
| 2015/0297466 A1* | 10/2015 | Jahns | A61K 8/26 428/312.8 |

FOREIGN PATENT DOCUMENTS

| | | |
|---|---|---|
| WO | WO 2011/082022 | 7/2011 |
| WO | WO 2012/066507 | 5/2012 |

OTHER PUBLICATIONS

PCT International Search Report for PCT/US2013/053181 mailed on Oct. 10, 2013.

\* cited by examiner

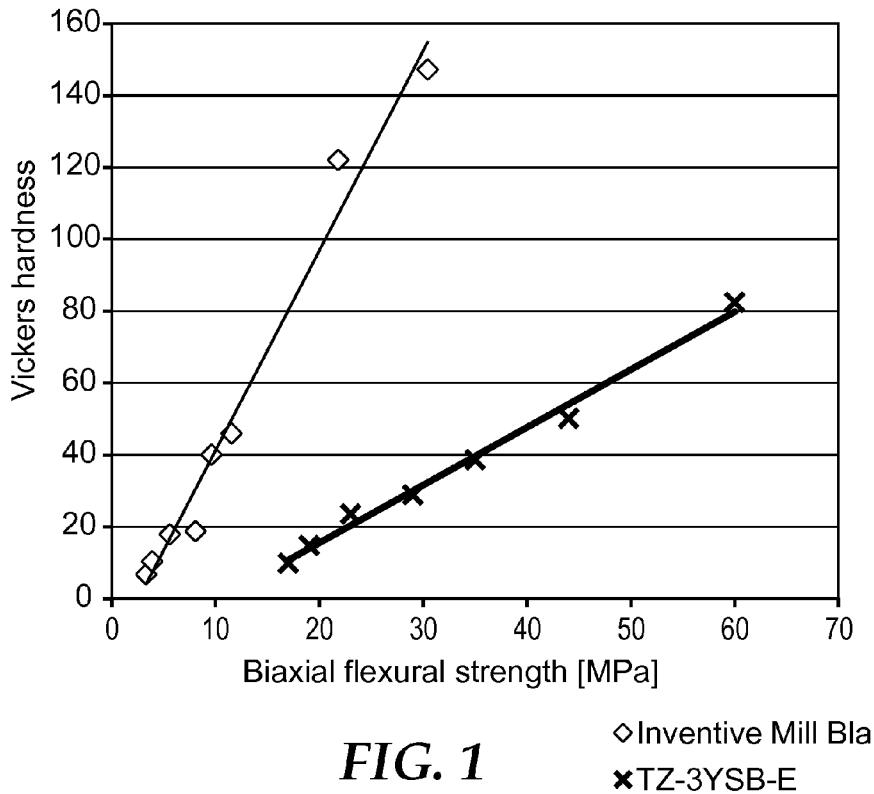
FIG. 1    ◇ Inventive Mill Blank
         × TZ-3YSB-E
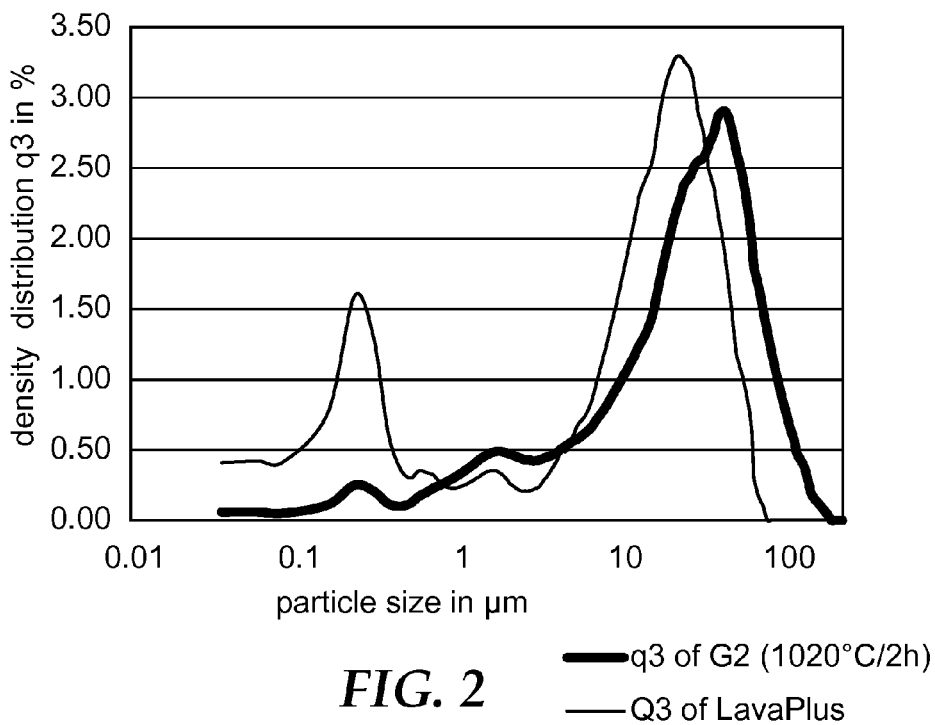
FIG. 2   ▬ q3 of G2 (1020°C/2h)
         — Q3 of LavaPlus

DENTAL BLANK COMPRISING A PRE-SINTERED POROUS ZIRCONIA MATERIAL, PROCESS OF ITS PRODUCTION AND DENTAL ARTICLE FORMED FROM SAID DENTAL BLANK

CROSS REFERENCE TO RELATED APPLICATIONS

This application is a national stage filing under 35 U.S.C. 371 of PCT/US2013/053181, filed 1 Aug. 2013, which claims priority to European Application No. 12179125.5, filed 3 Aug. 2012, the disclosure of which is incorporated by reference in its/their entirety herein.

FIELD OF THE INVENTION

The invention relates to a process of producing a dental article from a zirconia ceramic dental mill blank and to a dental article (e.g. in the shape of a crown or bridge or substructure thereof) obtainable by such a process.

BACKGROUND ART

A standard procedure to manufacture highly esthetic dental restorations based on zirconia is milling pre-sintered zirconia mill blanks with an exactly defined shrinkage and fire that work piece to final density and wanted dimensions. The quality of the milled structure typically depends on the bending strength of the mill blank used. The bending strength of the mill blank can be determined e. g. using a punch-on-3-balls test according the ISO standard 6872.

For grinding with e. g. diamonded burrs the bending strength of the mill block is typically from 60 MPa up to final strength of zirconia with a preferred upper limit round about 110 MPa. Grinding can be performed e.g. with grinding machines like CEREC™ InLab (Sirona Corp.) and E4D (D4D Corp.).

Milling can typically be performed if the bending strength of the mill block is within a range of 15 to 50 MPa. Milling can be done using e.g. the Lava™ system of 3M ESPE.

In EP 1 206 223 A1 (3M ESPE) it is outlined that for milling the raw breaking resistance of the dental mill blanks is usually within a range of 15 MPa to 30 MPa. If milling is performed outside these ranges, the obtained structure is often not milled adequately and may show chipping.

In US 2004/0119180 A1 (3M ESPE) a process of producing a denture comprising the steps of providing a mill blank having a raw breaking resistance of 31 to 50 MPa, milling the blank and sintering the milled blank is described.

U.S. Pat. No. 5,702,650 (Hintersehr) a process for producing ceramic dental prostheses are described by shaping a porous unfinished piece made out of ZrO2, Y2O3, HfO2, dense sintering or infiltration of the unfinished piece and reworking the unfinished piece by means of a rotating tool is described.

In U.S. application 61/545,243 (3M IPC) aerogels, calcined and crystalline articles and methods of making the same are described. The content of this application is herewith incorporated by reference.

US 2011/0269618 (Knapp et al.) relates to nano-crystalline dental ceramics, where the nanocrystals are formed by vaporization.

However, there is still room for improvement especially with regard to the requirements to be fulfilled with respect to modern dental materials.

DESCRIPTION OF THE INVENTION

A typical problem with state of the art zirconia mill blocks is the stickiness of the dust generated during the dry milling process which may lead to adhered dust on machine parts as well as on milled articles. An adherence of the dust to the milling burrs can become critical and can lead to a full clogging of the bur. This may result in a damage of the milled restoration. In order to reduce the dust and to minimize the related issues pressurized air cleaning is typically implemented in the milling machines.

Thus, it would be desirable to have a dental mill blank available with a more favourable machining behaviour (e.g. producing less milling dust during the machining process and/or being able to be milled and ground and/or being able to be machined more efficiently).

Alternatively or in addition, it would be desirable if the shape and/or surface of the machined dental article can be adjusted manually in an easy and reliable manner, if needed or desired.

This object can be achieved by a dental mill blank comprising a porous zirconia material being characterized by the following features:
 showing a $N_2$ adsorption and/or desorption of isotherm type IV according to IUPAC classification,
 having a Vickers hardness from about 25 to about 150 or from about 25 to about 140, the dental mill blank comprising means for reversible attaching it to a machining device.

In another embodiment the present invention features a process of producing a zirconia dental article comprising the steps of
 providing a dental mill blank comprising a porous zirconia material as described in the present text,
 placing the dental mill blank in a machining device,
 machining the porous zirconia material,
wherein the dental mill blank and the zirconia ceramic material is as described in the present text.

A further embodiment of the invention is directed to a dental article obtainable by a process as described in the present text.

DEFINITIONS

The term "dental article" means any article which can or is to be used in the dental or orthodontic field, especially for producing of or as dental restoration, a tooth model and parts thereof.

Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons) and parts thereof.

The surface of a tooth is considered not to be a dental article.

A dental article should not contain components which are detrimental to the patient's health and thus free of hazardous and toxic components being able to migrate out of the dental article.

"Monolithic dental restoration" shall mean a dental ceramic article onto the surface of which no facing or veneer has been attached. That is, the monolithic dental restoration is essentially comprised out of only one material composition. However, if desired a thin glazing layer can be applied.

By "dental mill blank" is meant a solid block (3-dim article) of material from which a dental article, dental workpiece, dental support structure or dental restoration can be machined in any subtractive process, e.g. besides milling also by grinding, drilling etc. A dental mill blank may have a size of about 20 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. A typical size of a blank as it is used for making a single crown has a diameter of about 24 mm and a length of about 19 mm. Further, a typical size of a blank as it is used for making bridges has a diameter of about 24 mm and a length of about 58 mm. Besides the above mentioned dimensions, a dental mill blank may also have the shape of a cube, a cylinder or a cuboid. Larger mill blanks may be advantageous if more than one crown or bridge should be manufactured out of one blank. For these cases, the diameter or length of a cylindric or cuboid shaped mill blank may be in a range of about 100 to about 200 mm, with a thickness being in the range of about 10 to about 30 mm.

"Zirconia ceramic article" shall mean a 3-dimensional article wherein at least one the x,y,z dimension is at least about 5 mm, the article being comprised of at least about 80 wt.-% zirconia.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former.

The porous ceramic dental material described in the present text does not contain a glass.

"Glass-ceramic" means an inorganic non-metallic material where one or more crystalline phases are surrounded by a glassy phase so that the material comprises a glass material and a ceramic material in a combination or mixture. It is formed as a glass, and then made to crystallize partly by heat treatment. Glass ceramics may refer to a mixture of lithium-, silicon-, and aluminium-oxides.

The porous dental material described in the present text does not contain a glass-ceramic.

"Sol" refers to a continuous liquid phase containing discrete particles having sizes in a range from 1 nm to 100 nm.

A "powder" means a dry, bulk composed of a large number of fine particles that may flow freely when shaken or tilted.

A "particle" means a substance being a solid having a shape which can be geometrically determined. The shape can be regular or irregular. Particles can typically be analysed with respect to e.g. grain size and grain size distribution.

"Ceramic" means an inorganic non-metallic material that is produced by application of heat. Ceramics are usually hard, porous and brittle and, in contrast to glasses or glass ceramics, display an essentially purely crystalline structure.

"Crystalline" means a solid composed of atoms arranged in a pattern periodic in three dimensions (i.e., has long range crystal structure as determined by X-ray diffraction). Crystal structures include tetragonal, monocline, cubic zirconia and mixtures thereof.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between about 15% and about 75% or between about 18% and about 75%, or between about 30% and about 70%, or between about 34% and about 67%, or between about 40% to about 68%, or between about 42% and about 67%.

The term "closed-celled" relates to a "closed porosity". Closed cells are those cells which are not accessible from the outside and cannot be infiltrated by gases under ambient conditions.

The "average connected pore diameter" means the average size of the open-celled pores of a material. The average connected pore diameter can be calculated as described in the Examples section.

The term "calcining" refers to a process of heating solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. Sintering typically includes the densification of a porous material to a less porous material (or a material having less cells) having a higher density, in some cases sintering may also include changes of the material phase composition (for example, a partial conversion of an amorphous phase toward a crystalline phase). "Diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size.

The term "aerogel" shall mean a three-dimensional low density (i.e., less than 20% of theoretical density) solid. An aerogel is a porous material derived from a gel, in which the liquid component of the gel has been replaced with a gas. The solvent removal is often done under supercritical conditions. During this process the network does not substantially shrink and a highly porous, low-density material can be obtained.

By "machining" is meant milling, grinding, drilling, cutting, carving, or substractive shaping a material by a machine. Milling is usually faster and more cost effective than grinding. A "machinable article" is an article having a 3-dimensional shape and having sufficient strength to be machined.

"Isotropic sintering behaviour" means that the sintering of a porous body during the sintering process occurs essentially invariant with respect to the directions x, y and z. "Essentially invariant" means that the difference in sintering behaviour with respect to the directions x, y and z is in a range of not more than about +/−5% or +/−2% or +/−1%.

The term "tubular reactor" refers to the portion of a continuous hydrothermal reactor system that is heated (i.e., the heated zone). The tubular reactor can be in any suitable shape. The shape of the tubular reactor is often selected based on the desired length of the tubular reactor and the method used to heat the tubular reactor. For example, the tubular reactor can be straight, U-shaped, or coiled. The interior portion of the tubular reactor can be empty or can contain baffles, balls, or other known mixing techniques.

"Casting" means a manufacturing process by which a liquid material (e.g. solution or dispersion) is poured into a mould, which contains a hollow cavity of the desired shape, and then allowed to solidify.

A composition is "essentially or substantially free of" a certain component, if the composition does not contain said component as an essential feature. Thus, said component is not willfully added to the composition either as such or in combination with other components or ingredient of other components. A composition being essentially free of a certain component usually contains the component in an amount of less than about 2 wt.-% or less than about 1 wt.-% or less than about 0.1 wt.-% or less than about 0.01 wt.-% with respect to the whole composition or material. The composition may not contain the said component at all. However, sometimes the presence of a small amount of the said component is not avoidable e.g. due to impurities.

"Ambient conditions" mean the conditions which the inventive solution is usually subjected to during storage and handling. Ambient conditions may, for example, be a pressure of about 900 to about 1100 mbar, a temperature of about 10 to about 40° C. and a relative humidity of about 10 to about 100%. In the laboratory ambient conditions are adjusted to about 20 to about 25° C. and about 1000 to about 1025 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Adding an "(s)" to a term means that the term should include the singular and plural form. E.g. the term "additive(s)" means one additive and more additives (e.g. 2, 3, 4, etc.).

BRIEF DESCRIPTION OF FIGURES

FIG. 1 shows the dependency of hardness and biaxial flexural strength of the porous dental ceramic material described in the present text and a porous dental ceramic material according to the state of the art.

FIG. 2 shows the volume related particle size distribution of milling dust of Lava™ Plus material (red curve) vs. material described in the present text (green curve).

DETAILED DESCRIPTION OF THE INVENTION

Figure 3:
FIG. 3 shows machined articles submersed and sonicated in an ultrasonic bath in de-mineralized water.

It has been found that the porous zirconia dental mill blank described in the present text fulfils the practitioners' needs especially with regard to the need for efficiently producing a dental article by a machining process.

The material described in the present text is in particular useful for producing monolithic dental articles.

The porous zirconia material of the dental mill blank described in the present text is characterized by a beneficial combination of features and/or parameters, e.g. adequate porosity and sufficient hardness.

Surprisingly it was found that a material showing a N2 adsorption and/or desorption of isotherm type IV (according to IUPAC classification) and/or adsorption desorption isotherms with a hysteresis loop (especially in a $p/p_0$ range of 0.70 to 0.95) are particularly suitable for producing an aesthetic dental article in an efficient way.

Commercially available Y-TZP ceramic materials typically show a N2 adsorption and/or desorption of isotherm type II (according IUPAC classification), which was found to be less effective for producing an aesthetic dental article in an efficient way.

Materials showing a type II isotherm are said to be macro-porous, whereas materials showing a type IV isotherm are said to be meso-porous.

Without wishing to be bound to a particular theory it is assumed that the stability and milling behaviour of a material is influenced by the type of pores.

It was found that a material having meso-pores (and showing a type IV isotherm and/or hysteresis loop) can be machined more reliable than a material having macro-pores (and showing a type II isotherm), e.g. if the edge stability is taken into consideration.

The dental mill blanks described in the present text enables the practitioner to produce dental articles in an easier and more efficient way.

It was found that the machining behaviour of the porous zirconia ceramic material is rather related to the Vickers hardness of the material than the biaxial flexural strength.

The material described in the present text can easily be shaped into a dental article. The shaping can be done with a machine or manually. It was found that machining can not only be done by milling but also by grinding. In contrast to this, commercially available zirconia materials are usually machined using a milling device but not a grinding device.

If desired, the dental article obtained after machining the material described in the present text can be further individualized manually, e.g. using a file, a cutter or carving tool. The material (before sintering) is sufficiently hard to allow a precise machining but not too hard or too strong to prevent manually individualization.

In contrast to this, commercially available zirconia materials are often too soft and thus allow no precise carving or modelling in a pre-sintered stage.

The material described in the present text can also be easily and reliably be adapted to be reversibly fixed into a machining device. For example, this can be done by carving notches, recesses or grooves into the material.

Further, it was found that during the machining of the material of the dental mill block and/or during the manual individualization of the machined dental article described in the present text, less dust is produced, which may adhere to either the machining tools and/or the surface of the machined dental article.

In contrast to this, when machining mill block of the state of the art it has been observed that various machine parts like suction grid, inner walls of milling chamber, frame holder are visibly covered with a thin layer of milling dust. In contrast to this, when machining the material of the mill block described in the present text the contamination of the machine parts with adhered milling dust was remarkably reduced.

Without wishing to be bound to a particular theory, it is believed that the favourable behaviour as regards the limited production of milling dust during milling can be related to its particle size distribution.

Unlike the milling dust obtained when machining mill blocks of the state of the art, the milling dust obtained when machining the material described in the present text shows a particle size distribution containing no or only a low fraction of particles smaller than 1 μm.

Further, it was found that during a manual adjustment or modification of the surface of the machined dental article, less milling dust adhered to the surface of the machined dental article when the material described in the present text was used (compared to using a material of the state of the art).

This will help to increase the productivity of the overall dental lab workflow since the often tedious cleaning steps needed to remove the adhered dust from the machined article (e.g. using brushes and/or pressurized air) can be reduced or are easier and faster to conduct.

The risk of failing to sufficiently remove the milling dust from the machined article—especially at the inner side of the dental restoration—combined with the risk to get a worse fit of the dental restoration to a prepared tooth surface is reduced.

Thus, using the material described in the present text will facilitate the production of high quality dental restoration(s).

The material described in the present text shows a variety of well balanced features (e.g. sufficient strength to be machined, adequate strength to be manually individualized, reduced wear wear of machining tools and/or reduced production of dust during machining).

The dental mill blank described in the present text comprises a porous zirconia material. The porous zirconia material shows a N2 adsorption and/or desorption of isotherm type IV according to IUPAC classification.

Further, the porous zirconia material has a Vickers hardness from about 25 to about 150 or from about 35 (HV 0.5) to about 150 (HV 1).

The dental mill blank also comprises means for reversible attaching it to a machining device.

According to one embodiment, the porous zirconia article described in the present text can be characterized by at least one of the following features:

(a) showing a $N_2$ adsorption and/or desorption isotherm with a hysteresis loop;

(b) showing a $N_2$ adsorption and desorption of isotherm type IV according to IUPAC classification and a hysteresis loop;

(c) showing a $N_2$ adsorption and desorption isotherm of type IV with a hysteresis loop of type H1 according to IUPAC classification;

(d) showing a $N_2$ adsorption and desorption isotherm of type IV with a hysteresis loop of type H1 according to IUPAC classification in a $p/p_0$ range of 0.70 to 0.95;

(e) average connected pore diameter: from about 10 to about 100 nm or from about 10 to about 80 nm or from about 10 to about 70 nm or from about 10 to about 50 nm or from about 15 to about 40;

(f) average grain size: less than about 100 nm or less than about 80 nm or less than about 60 nm or from about 10 to about 100 or from about 15 to about 60 nm;

(g) BET surface: from about 10 to about 200 $m^2/g$ or from about 15 to about 100 $m^2/g$ or from about 16 to about 60 $m^2/g$;

(h) Biaxial flexural strength: from about 10 to about 40 or from about 15 to about 30 MPa;

(i) x, y, z dimension: at least about 5 mm or at least about 10 or at least about 20 mm;

(j) Vickers hardness: from about 25 (HV 0.5) to about 150 or from about 35 to about 140 (HV 1).

A combination of the following features was found to be particularly beneficial: (a) and (h), or (a) and (b) and (h), or (b) and (c), or (c), (e), (g) and (h).

If desired the above features can be determined as described in the Example section.

Surprisingly it was found that material showing a $N_2$ adsorption and/or desorption of isotherm type IV (according to IUPAC classification) and/or adsorption desorption isotherms with a hysteresis loop (especially in a $p/p_0$ range of 0.70 to 0.95) are particularly suitable.

The BET surface of porous zirconia materials described in the prior art is typically within a range from 2 to 9 $m^2/g$, whereas the BET surface of the porous zirconia materials described in the present text is preferably above 10 $m^2/g$.

The average grain size of the zirconia particles in the porous zirconia article described in the present text is small compared to the average grain size of the material of commercially available mill blanks.

A small grain size can be beneficial in that it typically leads to a more homogeneous material (from a chemical perspective), which may also result in more homogeneous physical properties.

Thus, the porous zirconia article described in the present text has a unique combination of features, which facilitates a reliable production of highly aesthetic ceramic articles, especially with respect to edge stability.

Useful ranges for the x, y and z dimensions include from about 5 to about 300 or from about 8 to about 200 mm.

It was found that it is beneficial for certain properties, if the porous zirconia material has a certain average connected pore diameter. The average connected pore diameter should be in a particular range. It should not be too small and also not be too large.

The porous zirconia material described in the present text and used for providing the dental mill blank has a smaller average connected pore diameter than porous zirconia ceramic material obtained by compacting zirconia powder, like 3Y-TZP powder from Tosoh Comp.

Due to the nano-scaled particle size and specific average connected pore diameter of the material used for producing the porous zirconia ceramic material of the dental mill blank, this material has a different sintering behaviour compared to the zirconia ceramic material of dental mill blanks which are commercially available (e.g. LAVA™ Frame from 3M ESPE) and other zirconia ceramics ceramics available on the dental market being typically produced by compacting and pressing zirconia powder (e.g. 3Y-TZP zirconia powder from Tosoh Comp.).

The Vickers hardness of the material is in a particular range.

If the Vickers hardness of the material is too low, the machinability could fall off in quality (edge chipping or breaking of the workpiece) as well as in the ease of manual reworking to individualize the frame of a dental restoration or a monolithic restoration as well.

If the Vickers hardness of the material is too high, the wear of the machining tools may increase in an uneconomic range or the tool could break and destroy the workpiece.

The biaxial flexural strength of the material is typically also in a particular range.

It was found that if the biaxial flexural strength of the material is too low, the material tends to crack during the milling process or during the manual finishing by a dental technician.

On the other hand, if the biaxial flexural strength of the material is too high, the processing of the material by a milling machine is often not possible with reasonable efforts. The milling tool used or the milled material often tend to chip or break. In such a case the shaping of the material had to be done by grinding, e.g. using a Cerec™ grinding machine (Sirona).

The porous zirconia ceramic material of the dental mill blank can be characterized by at least one of the following features:
  ZrO2 content: from about 70 to about 98 mol % or from about 80 to about 97 mol %;
  HfO2 content: from about 0 to about 2 mol % or from about 0.1 to about 1.8 mol %;
  Y2O3 content: from about 1 to about 15 mol % or from about 1.5 to about 10 mol % or from about 2 to about 5 mol %;
  Al2O3 content: from about 0 to about 1 mol % or from about 0.005 to about 0.5 mol % or from about 0.01 to about 0.1 mol %.

According to a further embodiment, the porous zirconia article has a composition being characterized by the following features:
  ZrO2 content: from about 90 to about 98 mol %,
  HfO2 content: from about 0 to about 2 mol %,
  Y2O3 content: from about 1 to about 5 mol %,
  Al2O3 content: from about 0 to about 0.1 mol %.

It was found that a higher Y2O3 content typically leads to an increase of the cubic crystal phase in the zirconia ceramic material after sintering the material to final density. A higher content of the cubic crystal phase may contribute to a better translucency.

According to a particular embodiment the porous zirconia article can be characterized by the following features:
  showing a N2 adsorption of isotherm type IV according to IUPAC classification,
  showing a N2 adsorption with a hysteresis loop in a p/p0 range of 0.70 to 0.95,
  average connected pore diameter: from about 15 to about 60,
  average grain size: less than about 100 nm,
  BET surface: from about 15 to about 100 m$^2$/g or from about 16 to about 60 m$^2$/g,
  Biaxial flexural strength: from about 10 to about 40 MPa,
  x, y, z dimension: at least about 5 mm,
  Vickers hardness: from about 25 to about 150,
  Density: from about 40% to about 60% of theoretical density.

The porous zirconia ceramic material of the dental mill blank usually has the shape of a disc or block (e.g. cuboid, cylinder).

The dental mill blank comprises means for attaching the blank to a machining device, especially to the clamping appliance(s) of such a device. Suitable means include groove(s), recess(es), notch(es), stamp(s) and combinations thereof.

In another embodiment, the dental mill blank is fixed to or contained in a holding device.

The holding device containing the dental mill blank may then function as a means for attaching the blank to a machining device.

Fixing of the mill blank to a holding device can be effected by clamping, gluing, screwing and combinations thereof. Useful holding devices include frames (open and closed) or stumps.

Using a holding device may facilitate the production of the dental article with a machining device.

Examples of useful holding devices are described in U.S. Pat. No. 8,141,217 B2 (Gubler et al.), WO 02/45614 A1 (ETH Zurich), DE 203 16 004 U1 (Stuehrenberg), U.S. Pat. No. 7,985,119 B2 (Basler et al.) or WO 01/13862 (3M). The content of these documents with respect to the description of the holding device is herewith incorporated by reference.

According to another embodiment, the porous zirconia material can be obtained by a process comprising the step of heat treating or calcining a zirconia aerogel.

The zirconia aerogel can typically be characterized by at least one of the following features:
a. comprising crystalline zirconia particles having an average primary particle size in a range from 2 nm to 50 nm or from about 2 nm to about 30 nm or from about 2 to about 20 or from about 2 to about 15 nm;
b. content of crystalline zirconia particles: at least about 85 mol.-%;
c. having an organic content of at least 3 wt.-% or within a range from about 3 to about 10 wt.-%;
d. x, y, z dimension: at least about 5 or at least about 8 or at least about 10 or at least about 20 mm.

A combination of the features (a) and (b) or (a) and (c) or (a), (b) and (c) can be preferred.

The heat treatment for obtaining the porous zirconia article is typically done under the following conditions:
  temperature: from about 900 to about 1100° C. or from about 950 to about 1090° C.; from about 975 to about 1080° C.;
  atmosphere: air or inert gas (e.g. nitrogen, argon);
  duration: until a density of about 40 to about 60% of the final density of the material has been reached.

The heat treatment or calcining can be conducted in one or more steps.

In a first heat treatment step a binder burn-out could be performed to remove all organic additives from previous process steps to obtain a so called "white body".

In a second heat treatment step the strength and/or the hardness of the white-body could be adjusted to the needs of the follow up processes like machining. In case of a machinable blank the sintering protocol should reflect the interaction of temperature with strength and/or hardness.

If the temperature is too low, the hardness and/or strength of the resulting article might be too low. This can cause problems during a later machining step, e.g. with respect to chipping.

If, on the other hand, the temperature is too high, the hardness and/or strength of the material may become too high. This can cause problems during a later machining step as well, e.g. with respect to the machining tool durability.

The dwell time (that is the time during which the aerogel is kept at that temperature) is helpful as well to tune strength and/or hardness to the specific needs of the chosen machining technology. The dwell time, however, can also be in a range from about 0 to about 24 h or from about 0.1 to about 5 h.

If the dwell time is too long, the dental mill blanks may become too hard to be machined under reasonable conditions.

According to one embodiment, the porous zirconia material of the dental mill blank or the porous zirconia article can be obtained by a process comprising the steps of
  providing a zirconia sol comprising crystalline metal oxide particles and a solvent,
  optionally concentrating the zirconia sol to provide a concentrated zirconia sol,
  mixing the sol with a polymerizable organic matrix (e.g. adding a reactive surface modifier to the zirconia sol and optionally an initiator being able to polymerizable surface-modified particles of the zirconia sol);
  optionally casting the zirconia sol into a mould to provide a casted zirconia sol,
  curing the polymerizable organic matrix of the zirconia sol to form a gel (sometimes also referred to as gelation step),
  removing the solvent from the gel (e.g. by first removing water, if present, from the gel via a solvent exchange process to provide an at least partially de-watered gel; followed by a further extraction step where the remaining solvent is extracted e.g. via super critical extraction) to provide the aerogel,
  optionally cutting the aerogel into smaller pieces,
  heat-treating the aerogel to obtain e.g. a machinable material or article.

The process of producing the porous ceramic zirconia material typically starts with providing a sol of ZrO2 particles.

To the sol of ZrO2 particles a surface-modifying agent is added, preferably a crosslinkable surface-modifying agent (e.g. a radically reactive surface modifier).

The ZrO2 particles having been surface-modified with a crosslinkable agent can be polymerized, if desired, to provide a composition comprising crosslinked ZrO2 particles.

The crosslinkable surface-modifying agent can be removed later, e.g. during a calcining and/or pre-sintering step.

If desired, the sol is casted into a mould. The mould may have the negative shape of the dental mill block to be provided. Due to size reduction which may be caused by heat treatments of the material, the size of the mould is typically larger than the size of the final dental mill blank.

The shape of the mould is not particularly limited.

The casted zirconia sol is typically treated with heat or radiation in order to start polymerization of the reactive surface modifier. This process usually results in a gel. If present and desired, water may be removed from the gel, at least partially.

Remaining solvent of the above described sol/gel process is removed, e.g. by supercritical extraction techniques resulting in an aerogel (e.g. in block form).

If desired, the aerogel may be cut into smaller pieces, e.g. having the shape of the dental mill blank.

Zirconia sols are dispersions of zirconia based ceramic particles. The zirconia in the zirconia-based ceramic particles is crystalline, and has been observed to be cubic, tetragonal, monoclinic, or a combination thereof. Because the cubic and tetragonal phases are difficult to differentiate using x-ray diffraction techniques, these two phases are typically combined for quantitative purposes and are referred to as the cubic/tetragonal phase. "Cubic/tetragonal" or "C/T" is used interchangeably to refer to the cubic plus the tetragonal crystalline phases. The percent cubic/tetragonal phase can be determined, for example, by measuring the peak area of the x-ray diffraction peaks for each phase and using Equation (I).

$$\% \ C/T = 100(C/T) \div (C/T + M) \qquad (I)$$

In Equation (I), C/T refers to the peak area of the diffraction peak for the cubic/tetragonal phase, M refers to the peak area of the diffraction peak for the monoclinic phase, and % C/T refers to the weight percent cubic/tetragonal crystalline phase. The details of the x-ray diffraction measurements are described more fully in the Example section below.

Typically, at least 50 (in some embodiments, at least 55, 60, 65, 70, 75, 80, 85, 90, or at least 95) weight percent of the zirconia-based particles are present in the cubic or tetragonal crystal structure (i.e., cubic crystal structure, tetragonal crystal structure, or a combination thereof). A greater content of the cubic/tetragonal phase is often desired.

The zirconia particles in the zirconia sols described herein typically have primary particle size in a range of from 2 nm to 50 nm (in some embodiments, 5 nm to 50 nm, 2 nm to 25 nm, 5 nm to 25 nm, 2 nm to 15 nm, or even 5 nm to 15 nm).

Depending on how the zirconia-based particles are prepared, the particles may contain at least some organic material in addition to the inorganic oxides. For example, if the particles are prepared using a hydrothermal approach, there may be some organic material attached to the surface of the zirconia-based particles. Although not wanting to be bound by theory, it is believed that organic material originates from the carboxylate species (anion, acid, or both) included in the feedstock or formed as a byproduct of the hydrolysis and condensation reactions (i.e., organic material is often absorbed on the surface of the zirconia-based particles). For example, in some embodiments, the zirconia-based particles contain up to 15 (in some embodiments, up to 12, 10, 8, or even up to 6) weight percent organic material, based on the weight of the particles.

Although any of a variety of known methods can be used to provide the zirconia-based particles, preferably they are prepared using hydrothermal technology. In one exemplary embodiment, the zirconia-based sols are prepared by hydrothermal treatment of aqueous metal salt (e.g., a zirconium salt, an yttrium salt, and an optional lanthanide element salt or aluminum salt) solutions, suspensions or a combination of them.

The aqueous metal salts, which are selected to be soluble in water, are typically dissolved in the aqueous medium. The aqueous medium can be water or a mixture of water with other water soluble or water miscible materials. In addition, the aqueous metal salts and other water soluble or water miscible materials which may be present are typically selected to be removable during subsequent processing steps and to be non-corrosive.

At least a majority of the dissolved salts in the feedstock are usually carboxylate salts rather than halide salts, oxyhalide salts, nitrate salts, or oxynitrate salts. Although not wanting to be bound by theory, it is believed that halide and nitrate anions in the feedstock tend to result in the formation of zirconia-based particles that are predominately of a monoclinic phase rather than the more desirable tetragonal or cubic phases. Further, carboxylates and/or acids thereof tend to be more compatible with an organic matrix material compared to halides and nitrates. Although any carboxylate anion can be used, the carboxylate anion often has no greater than 4 carbon atoms (e.g., formate, acetate, propionate, butyrate, or a combination thereof). The dissolved salts are often acetate salts. The feedstock can further include, for example, the corresponding carboxylic acid of the carboxylate anion. For example, feedstocks prepared from acetate salts often contain acetic acid.

One exemplary zirconium salt is zirconium acetate salt, represented by a formula such as $ZrO((4-n)/2)n+ (CH3COO-)n$, where n is in the range from 1 to 2. The zirconium ion may be present in a variety of structures depending, for example, on the pH of the feedstock. Methods of making zirconium acetate are described, for example, in W. B. Blumenthal, "The Chemical Behavior of Zirconium," pp. 311-338, D. Van Nostrand Company, Princeton, N.J. (1958). Suitable aqueous solutions of zirconium acetate are commercially available, for example, from Magnesium Elektron, Inc., Flemington, N.J., that contain, for example, up to 17 weight percent zirconium, up to 18 weight percent zirconium, up to 20 weight percent zirconium, up to 22 weight percent, up to 24 weight percent, up to 26 weight percent, and up to 28 weight percent zirconium, based on the total weight of the solution.

Similarly, exemplary yttrium salts, lanthanide element salts, and aluminum salts often have a carboxylate anion, and are commercially available. Because these salts are typically used at much lower concentration levels than the zirconium salt, however, salts other than carboxylate salts (e.g., acetate salts) may also be useful (e.g., nitrate salts).

The total amount of the various salts dissolved in the feedstock can be readily determined based on the total percent solids selected for the feedstock. The relative amounts of the various salts can be calculated to provide the selected composition for the zirconia-based particles.

Typically, the pH of the feedstock is acidic. For example, the pH is usually less than 6, less than 5, or even less than 4 (in some embodiments, in a range from 3 to 4).

The liquid phase of the feedstock is typically predominantly water (i.e., the liquid phase is an aqueous based medium). Preferably, the water is deionized to minimize the introduction of alkali metal ions, alkaline earth ions, or both into the feedstock. Optionally, water-miscible organic co-solvents are included in the liquid phase in amounts, for example, up 20 weight percent, based on the weight of the liquid phase. Suitable co-solvents include 1-methoxy-2-propanol, ethanol, isopropanol, ethylene glycol, N,N-dimethylacetamide, and N-methyl pyrrolidone.

When subjected to hydrothermal treatment, the various dissolved salts in the feedstock undergo hydrolysis and condensation reactions to form the zirconia-based particles. These reactions are often accompanied with the release of an acidic byproduct. That is, the byproduct is often one or more carboxylic acids corresponding to the zirconium carboxylate salt plus any other carboxylate salt in the feedstock. For example, if the salts are acetate salts, acetic acid is formed as a byproduct of the hydrothermal reaction.

Any suitable hydrothermal reactor can be used for the preparation of the zirconia-based particles. The reactor can be a batch or continuous reactor. The heating times are typically shorter and the temperatures are typically higher in a continuous hydrothermal reactor compared to a batch hydrothermal reactor. The time of the hydrothermal treatments can be varied depending, for example, on the type of reactor, the temperature of the reactor, and the concentration of the feedstock. The pressure in the reactor can be autogeneous (i.e., the vapor pressure of water at the temperature of the reactor), can be hydraulic (i.e., the pressure caused by the pumping of a fluid against a restriction), or can result from the addition of an inert gas such as nitrogen or argon. Suitable batch hydrothermal reactors are available, for example, from Parr Instruments Co., Moline, Ill. Some suitable continuous hydrothermal reactors are described, for example, in U.S. Pat. Nos. 5,453,262 (Dawson et al.) and 5,652,192 (Matson et al.); Adschiri et al., J. Am. Ceram. Soc., 75, 1019-1022 (1992); and Dawson, Ceramic Bulletin, 67 (10), 1673-1678 (1988).

In some embodiments, the feedstock is passed through a continuous hydrothermal reactor. As used herein, the term "continuous" with reference to the hydrothermal reactor system means that the feedstock is continuously introduced and an effluent is continuously removed from the heated zone. The introduction of feedstock and the removal of the effluent typically occur at different locations of the reactor. The continuous introduction and removal can be constant or pulsed.

The dimensions of tubular reactor can be varied and, in conjunction with the flow rate of the feedstock, can be selected to provide suitable residence times for the reactants within the tubular reactor. Any suitable length tubular reactor can be used provided that the residence time and temperature are sufficient to convert the zirconium in the feedstock to zirconia-based particles. The tubular reactor often has a length of at least 0.5 meter (in some embodiments, at least 1 meter, 2 meters, 5 meters, 10 meters, 15 meters, 20 meters, 30 meters, 40 meters, or even at least 50 meters). The length of the tubular reactor in some embodiments is less than 500 meters (in some embodiments, less than 400 meters, 300 meters, 200 meters, 100 meters, 80 meters, 60 meters, 40 meters, or even less than 20 meters).

Tubular reactors with a relatively small inner diameter are sometimes preferred. For example, tubular reactors having an inner diameter no greater than about 3 centimeters are often used because of the fast rate of heating of the feedstock that can be achieved with these reactors. Also, the temperature gradient across the tubular reactor is less for reactors with a smaller inner diameter compared to those with a larger inner diameter. The larger the inner diameter of the tubular reactor, the more this reactor resembles a batch reactor. However, if the inner diameter of the tubular reactor is too small, there is an increased likelihood of the reactor becoming plugged or partially plugged during operation resulting from deposition of material on the walls of the reactor. The inner diameter of the tubular reactor is often at least 0.1 cm (in some embodiments, at least 0.15 cm, 0.2 cm, 0.3 cm, 0.4 cm, 0.5 cm, or even at least 0.6 cm). In some embodiments, the diameter of the tubular reactor is no greater than 3 cm (in some embodiments, no greater than 2.5 cm, 2 cm, 1.5 cm, or even greater than 1 centimeter; in some embodiments, in a range from 0.1 to 2.5 cm, 0.2 cm to 2.5 cm, 0.3 cm to 2 cm, 0.3 cm to 1.5 cm, or even 0.3 cm to 1 cm).

In a continuous hydrothermal reactor, the temperature and the residence time are typically selected in conjunction with the tubular reactor dimensions to convert at least 90 mole percent of the zirconium in the feedstock to zirconia-based particles using a single hydrothermal treatment. That is, at least 90 mole percent of the dissolved zirconium in the feedstock is converted to zirconia-based particles within a single pass through the continuous hydrothermal reactor system.

Alternatively, for example, a multiple step hydrothermal process can be used. For example, the feedstock can be subjected to a first hydrothermal treatment to form a zirconium-containing intermediate and a by-product such as a carboxylic acid. A second feedstock can be formed by removing at least a portion of the by-product of the first hydrothermal treatment from the zirconium-containing intermediate. The second feedstock can then be subjected to a second hydrothermal treatment to form a sol containing the zirconia-based particles. Further details on this process are described, for example, in U.S. Pat. No. 7,241,437 (Davidson et al.).

If a two step hydrothermal process is used, the percent conversion of the zirconium-containing intermediate is typically in a range from 40 to 75 mole percent. The conditions used in the first hydrothermal treatment can be adjusted to provide conversion within this range. Any suitable method can be used to remove at least part of the by-product of the first hydrothermal treatment. For example, carboxylic acids such as acetic acid can be removed by a variety of methods such as vaporization, dialysis, ion exchange, precipitation, and filtration.

When referring to a continuous hydrothermal reactor, the term "residence time" means the average length of time that the feedstock is within the heated portion of the continuous hydrothermal reactor system.

Any suitable flow rate of the feedstock through the tubular reactor can be used as long as the residence time is sufficiently long to convert the dissolved zirconium to zirconia-based particles. That is, the flow rate is often selected based on the residence time needed to convert the zirconium in the feedstock to zirconia-based particles. Higher flow rates are desirable for increasing throughput and for minimizing the deposition of materials on the walls of the tubular reactor. A higher flow rate can often be used when the length of the reactor is increased or when both the length and diameter of the reactor are increased. The flow through the tubular reactor can be either laminar or turbulent.

In some exemplary continuous hydrothermal reactors, the reactor temperature is in the range from 170° C. to 275° C., 170° C. to 250° C., 170° C. to 225° C., 180° C. to 225° C., 190° C. to 225° C., 200° C. to 225° C., or even 200° C. to 220° C. If the temperature is greater than about 275° C., the pressure may be unacceptably high for some hydrothermal reactors systems. However, if the temperature is less than about 170° C., the conversion of the zirconium in the feedstock to zirconia-based particles may be less than 90 weight percent using typical residence times.

The effluent of the hydrothermal treatment (i.e., the product of the hydrothermal treatment) is a zirconia-based sol. The sol contains at least 3 weight percent zirconia-based particles dispersed, suspended, or a combination thereof in an aqueous medium. In some embodiments, the zirconia-based particles can contain (a) 0 to 5 mole percent of a lanthanide element oxide, based on total moles of inorganic oxide in the zirconia-based particles, and (b) 1 to 15 mole percent yttrium oxide, based on total moles of inorganic oxide in the zirconia-based particles. The zirconia-based particles are crystalline and have an average primary particle size no greater than 50 nanometers. In some embodiments, cerium oxide, magnesium oxide, ytterbium oxide, and/or calcium oxide may be used with or in place of the yttria.

In some embodiments, at least a portion of the aqueous-based medium is removed from the zirconia-based sol. Any known means for removing the aqueous-based medium can be used. This aqueous-based medium contains water and often contains dissolved carboxylic acids and/or anions thereof that are present in the feedstock or that are byproducts of the reactions that occur within the hydrothermal reactor. As used herein, the term "carboxylic acids and/or anions thereof" refers to carboxylic acids, carboxylate anions of these carboxylic acids, or mixtures thereof. The removal of at least a portion of these dissolved carboxylic acids and/or anions thereof from the zirconia-based sol may be desirable in some embodiments. The zirconia-based sol can be subjected, for example, to at least one of vaporization, drying, ion exchange, solvent exchange, diafiltration, or dialysis, for example, for concentrating, removal of impurities or to compatibilize with other components present in the sol.

In some embodiments, the zirconia sol (prepared from hydrothermal process or other processes) is concentrated. Along with removing at least a portion of the water present in the effluent, the concentration or drying process often results in the vaporization of at least a portion of the dissolved carboxylic acids.

In other embodiments, for example, the zirconia based sol can be subjected to dialysis or diafiltration. Dialysis and diafiltration both tend to remove at least a portion of the dissolved carboxylic acids and/or anions thereof. For dialysis, a sample of the effluent can be positioned within a membrane bag that is closed and then placed within a water bath. The carboxylic acid and/or carboxylate anions diffuse out of the sample within the membrane bag. That is, these species will diffuse out of the effluent through the membrane bag into the water bath to equalize the concentration within the membrane bag to the concentration in the water bath. The water in the bath is typically replaced several times to lower the concentration of species within the bag. A membrane bag is typically selected that allows diffusion of the carboxylic acids and/or anions thereof but does not allow diffusion of the zirconia-based particles out of the membrane bag.

For diafiltration, a permeable membrane is used to filter the sample. The zirconia particles can be retained by the filter if the pore size of the filter is appropriately chosen. The dissolved carboxylic acids and/or anions thereof pass through the filter. Any liquid that passes through the filter is replaced with fresh water. In a discontinuous diafiltration process, the sample is often diluted to a pre-determined volume and then concentrated back to the original volume by ultrafiltration. The dilution and concentration steps are repeated one or more times until the carboxylic acid and/or anions thereof are removed or lowered to an acceptable concentration level. In a continuous diafiltration process, which is often referred to as a constant volume diafiltration process, fresh water is added at the same rate that liquid is removed through filtration. The dissolved carboxylic acid and/or anions thereof are in the liquid that is removed.

While the majority of the yttrium and lanthanum, if present, are incorporated into the crystalline zirconia particles there is a fraction of these metals that can be removed during the diafiltration or dialysis process. The actual composition of a sol after diafiltration may be different than that before dialysis.

A zirconia based sol comprises zirconia-based particles dispersed and/or suspended (i.e., dispersed, suspended, or a combination thereof) in an aqueous/organic matrix. In some embodiments, the zirconia-based particles can be dispersed and/or suspended in the organic matrix without any further surface modification. The organic matrix can be added directly to zirconia based sol. Also, for example, the organic matrix can be added to the zirconia based sol after treatment to remove at least some of the water, after treatment to remove at least some of the carboxylic acids and/or anions thereof, or after both treatments. The organic matrix that is added is often contains a polymerizable composition that is subsequently polymerized and/or crosslinked to form a gel.

In some embodiments, the zirconia based sol can be subjected to a solvent exchange process. An organic solvent having a higher boiling point than water can be added to the effluent. Examples of organic solvents that are suitable for use in a solvent exchange method include 1-methoxy-2-propanol and N-methyl pyrrolidone. The water then can be removed by a method such as distillation, rotary evaporation, or oven drying. Depending on the conditions used for removing the water, at least a portion of the dissolved carboxylic acid and/or anion thereof can also be removed. Other organic matrix material can be added to the treated effluent (i.e., other organic matrix material can be added to the zirconia-based particle suspended in the organic solvent used in the solvent exchange process).

In some embodiments, the zirconia-based sols are treated with a surface modification agent to improve compatibility with the organic matrix material. Surface modification agents may be represented by the formula A-B, where the A group is capable of attaching to the surface of a zirconia-based particle and B is a compatibility group. Group A can be attached to the surface by adsorption, formation of an ionic bond, formation of a covalent bond, or a combination thereof. Group B can be reactive or non-reactive and often tends to impart characteristics to the zirconia-based particles that are compatible (i.e., miscible) with an organic solvent, with another organic matrix material (e.g., monomer, oligomers, or polymeric material), or both. For example, if the solvent is non-polar, group B is typically selected to be non-polar as well. Suitable B groups include linear or branched hydrocarbons that are aromatic, aliphatic, or both aromatic and aliphatic. The surface modifying agents include carboxylic acids and/or anions thereof, sulfonic acids and/or anions thereof, phosphoric acids and/or anions thereof, phosphonic acids and/or anions thereof, silanes, amines, and alcohols. Suitable surface modification agents are further described, for example, in PCT Application Publication WO 2009/085926 (Kolb et al.), the disclosure of which is incorporated herein by reference.

A surface modification agent can be added to the zirconia-based particles using conventional techniques. The surface modification agent can be added before or after any removal of at least a portion of the carboxylic acids and/or anions thereof from the zirconia-based sol. The surface modification agent can be added before or after removal of the water from the zirconia-based sol. The organic matrix can be added before or after surface modification or simultaneously with surface modification. Various methods of adding the surface modification agent are further described, for example, in WO 2009/085926 (Kolb et al.), the disclosure of which is incorporated herein by reference.

The surface modification reactions can occur at room temperature (e.g., 20° C. to 25° C.) or at an elevated temperature (e.g., up to about 95° C.). When the surface modification agents are acids such as carboxylic acids, the zirconia-based particles typically can be surface-modified at room temperature. When the surface modification agents are silanes, the zirconia-based particles are typically surface modified at elevated temperatures.

The organic matrix typically includes a polymeric material or a precursor to a polymeric material such as a monomer or an oligomer having a polymerizable group and a solvent. The zirconia-based particles can be combined with the organic matrix using conventional techniques. For example, if the organic matrix is a precursor to a polymeric material, the zirconia-based particles can be added prior to the polymerization reaction. The composite material containing a precursor of a polymeric material is often shaped before polymerization.

Representative examples of monomers include (meth) acrylate-based monomers, styrene-based monomers, and epoxy-based monomers. Representative examples of reactive oligomers include, polyesters having (meth)acrylate groups, polyurethanes having (meth)acrylate groups, polyethers having (meth)acrylate groups, or acrylics. Representative examples of polymeric material include polyurethanes, poly(meth)acrylates, and polystyrenes.

The zirconia based sols are typically solidified by gelation. Preferably, the gelation process allows large gels to be formed without cracks and gels that can be further processed without inducing cracks. For example, preferably, the gelation process leads to a gel having a structure that will not collapse when the solvent is removed. The gel structure is compatible with and stable in a variety of solvents and conditions that may be necessary for supercritical extraction. Furthermore, the gel structure needs to be compatible with supercritical extraction fluids (e.g., supercritical $CO_2$). In other words, the gels should be stable and strong enough to withstand drying, so as to produce stable gels and give materials that can be heated to burn out the organics, pre-sintered, and densified without inducing cracks. Preferably, the resulting gels have relatively small and uniform pore size to aid in sintering them to high density at low sintering temperatures. However, preferably the pores of the gels are large enough to allow product gases of organic burnout escape without leading to cracking of the gel. Furthermore, the gelation step allows control of the density of the resulting gels aids in the subsequent processing of the gel such as supercritical extraction, organic burnout, and sintering. It is preferable that the gel contain the minimum amount of organic material or polymer modifiers.

The gels described herein contain zirconia-based particles. In some embodiments, the gels contain at least two types of zirconia-based particles varying in crystalline phases, composition, or particle size. We have found, particulate based gels can lead to less shrinkage compared to gels produced form alkoxides which undergo significant and complicated condensation and crystallization reactions during further processing. The crystalline nature allows combinations of different crystal phases on a nanoscale. Applicants have observed that formation of a gel thru polymerization of these reactive particles yield strong, resilient gels. Applicants have also found that the use of mixtures of sols with crystalline particles can allow formation of stronger and more resilient gels for further processing. For example, Applicants observed that a gel comprising a mixture of cubic and tetragonal zirconia particles was less susceptible to cracking during supercritical extraction and organic burnout steps.

The gels comprise organic material and crystalline metal oxide particles, wherein the crystalline metal oxide particles are present in a range from 3 to 20 volume percent, based on the total volume of the gel, wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. Optionally, the gels may also include amorphous non-crystalline oxide sources.

In some embodiments, gels described herein, the crystalline metal oxide particles have an average primary particle size in a range from 5 nanometers to 50 nanometers (in some embodiments, in a range from 5 nanometers to 25 nanometers, 5 nanometers to 15 nanometers, or even from 5 nanometers to 10 nanometers). Typically, the average primary particle size is measured by using the X-Ray Diffraction technique. Preferably, the particles are not agglomerated but, it is possible that particles with some degree of aggregation may also be useful.

Exemplary sources of the $ZrO_2$, $Y_2O_3$, $La_2O_3$, and $Al_2O_3$ include crystalline zirconia based sols prepared by any suitable means. The sols described above are particularly well suited. The $Y_2O_3$, $La_2O_3$, and $Al_2O_3$, can be present in the zirconia based particles, and/or present as separate colloidal particles or soluble salts.

In some embodiments, for gels described herein the crystalline metal oxide particles comprise a first plurality of particles, and a second, different plurality of particles (i.e., is distinguishable by average composition, phase(s), microstructure, and/or size).

Typically, gels described herein have an organic content that is at least 3 (in some embodiments, at least 4, 5, 10, 15, or even at least 20) percent by weight, based on the total weight of the gel. In some embodiments, gels described herein have an organic content in a range from 3 to 30, 10 to 30, or even 10 to 20, percent by weight, based on the total weight of the gel.

Optionally, gels described herein comprise at least one of $Y_2O_3$ (e.g., in a range from 1 to 15, 1 to 9, 1 to 5, 6 to 9, 3.5 to 4.5, or even 7 to 8 mole percent of the crystalline metal oxide is $Y_2O_3$), $La_2O_3$ (e.g., up to 5 mole percent $La_2O_3$), or $Al_2O_3$ (e.g., up to 0.5 mole percent $Al_2O_3$).

In one exemplary gel the crystalline metal oxide comprises in a range from 1 to 5 mole percent $Y_2O_3$, and in a range from 0 to 2 mole percent $La_2O_3$, and in a range from 93 to 97 mole percent $ZrO_2$. In another exemplary gel the crystalline metal oxide comprises in a range from 6 to 9 mole percent $Y_2O_3$, and in a range from 0 to 2 mole percent $La_2O_3$, and in a range from 89 to 94 mole percent $ZrO_2$. In another exemplary gel the crystalline metal oxide comprises in a range from 3.5 to 4.5 mole percent $Y_2O_3$, and in a range from 0 to 2 mole percent $La_2O_3$, and in a range from 93.5 to 96.5 mole percent $ZrO_2$. In another exemplary gel the crystalline metal oxide comprises in a range from 7 to 8 mole percent $Y_2O_3$, and in a range from 0 to 2 mole percent $La_2O_3$, and in a range from 90 to 93 mole percent $ZrO_2$. Other optional oxides that may be present in gels described herein include at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, $NiO$, $CuO$, $Bi_2O_3$, $Ga_2O_3$, or $Lu_2O_3$. Additives that may add desired coloring to the resulting crack free crystalline metal oxide articles include at least one of $Fe_2O_3$, $MnO_2$, $Co_2O_3$, $Cr_2O_3$, $NiO$, $CuO$, $Bi_2O_3$, $Ga_2O_3$, $Er_2O_3$, $Pr_2O_3$, $Eu_2O_3$, $Dy_2O_3$, $Sm_2O_3$, or $CeO_2$. In some embodiments, the amount of optional oxide(s) is in an amount in a range from about 10 ppm to 20,000 ppm. In some embodiments, it is desirable to have sufficient oxides present to so the crack free crystalline metal oxide articles has coloring of a tooth.

One exemplary method for making gels described herein comprises providing a first zirconia sol comprising crystalline metal oxide particles having an average primary particle size of not greater than 15 nanometers (in some embodiments, in a range from 5 nanometers to 15 nanometers), wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. The sol is optionally concentrated to provide a concentrated zirconia sol.

A co-solvent, surface modifiers and optional monomers are added while stirring to obtain a well dispersed sol. Also, a radical initiator (e.g., ultraviolet (UV) or thermal initiator) is added to the radically polymerizable surface-modified zirconia sol.

The resulting sol is optionally purged with $N_2$ gas to remove oxygen. The resulting sol can be gelled by radiating with actinic or heating at at least one temperature for a time sufficient to polymerize the radically surface-modified zirconia sol comprising the radical initiator to form a gel. Typically the resulting gel is a strong, translucent gel.

In some embodiments the sols for making aerogels described herein comprise zirconia based particles that are surface modified with a radically polymerizable surface treatment agent/modifier.

Exemplary radically polymerizable surface modifiers include acrylic acid, methacrylic acid, beta-carboxyethyl acrylate, and mono-2-(methacryloxyethyl)succinate. An exemplary modification agent for imparting both polar character and reactivity to the zirconia-containing nanoparticles is mono(methacryloxypolyethyleneglycol) succinate. Exemplary polymerizable surface modifiers can be can reaction products of hydroxyl containing polymerizable monomers with cyclic anhydrides such as succinic anhydride, maleic anhydride and pthalic anhydride. Exemplary polymerization hydroxyl containing monomers include hyroxyethyl acrylate, hydroxyethyl methacrylate, hydoxypropyl acrylate, hydoxyproyl methacrylate, hydroxyl butyl acrylate, and hydroxybutyl methacrylate. Acyloxy and methacryloxy factional polyethylene oxide, and polypropylene oxide may also be used as the polymerizable hydroxyl containing monomers. Exemplary polymerizable silanes include alkyltrialkoxysilanes methacryloxyalkyltrialkoxysilanes or acryloxyalkyltrialkoxysilanes (e.g., 3-methacryloxypropyltri-methoxysilane, 3-acryloxypropyltrimethoxysilane, and 3-(methacryloxy)propyltriethoxysilane; as 3-(methacryloxy)propylmethyldimethoxysilane, and 3-(acryloxypropyl)methyldimethoxysilane); methacryloxyalkyldialkylalkoxysilanes or acyrloxyalkyldialkylalkoxysilanes (e.g., 3-(methacryloxy)propyldimethylethoxysilane); mercaptoalkyltrialkoxylsilanes (e.g., 3-mercapto-propyltrimethoxysilane); aryltrialkoxysilanes (e.g., styrylethyltrimethoxysilane); vinylsilanes (e.g., vinylmethyldiacetoxysilane, vinyldimethylethoxysilane, vinylmethyldiethoxysilane, vinyltrimethoxysilane, vinyltriethoxysilane, vinyltriacetoxysilane, vinyltriisopropoxysilane, vinyltrimethoxysilane, and vinyltris(2-methoxyethoxy)silane).

Methods for adding a surface modification agent to the zirconia-containing nanoparticles are known in the art. The surface modification agent can be added, for example, before or after any removal of at least a portion of the carboxylic acids and/or anions thereof from the zirconia-containing sol. The surface modification agent can be added, for example, before or after removal of the water from the zirconia-containing sol. The organic matrix can be added, for example, after surface modification or simultaneously with surface modification.

In one exemplary embodiment, the gel is formed by radical polymerization of the surface modified particles and optional monomers.

The polymerization can be initiated by any suitable means such as thermally or actinic radiation or UV initiators. Exemplary thermal initiators include (2,2'-azobis(2-methylbutyronitrile) (available, for example, under the trade designation "VAZO 67" from E. I. du Pont de Nemours and Company, Wilmington, Del.), azobisisobututyronitrile (available, for example, under the trade designation "Vazo 64" from E. I. du Pont de Nemours and Company), 2,2'-azodi-(2,4-Dimethylvaleronitrile (available, for example, under the trade designation "Vazo 52" from E. I. du Pont de Nemours and Company), and 1,1'-azobis(cyclohexanecabonitrile) (available, for example, under the trade designation "Vazo 88" from E. I. du Pont de Nemours and Company). Peroxides and hydroperoxides (e.g., benzoyl peroxide and lauryl peroxide) may also be useful. The initiator selection may be influenced, for example, by solvent choice, solubility and desired polymerization temperature. A preferred initiator is the 2,2'-azobis(2-methylbutyronitrile) available from E. I. du Pont de Nemours and Company under the trade designation "VAZO 67").

Exemplary UV initiators include 1-hydroxycyclohexyl benzophenone (available, for example, under the trade designation "IRGACURE 184" from Ciba Specialty Chemicals Corp., Tarrytown, N.Y.), 4-(2-hydroxyethoxyl)phenyl-(2-hydroxy-2-propyl) ketone (available, for example, under the trade designation "IRGACURE 2529" from Ciba Specialty Chemicals Corp.), 2-hydroxy-2-methylpropiophenone (available, for example, under the trade designation "DAROCURE D111" from Ciba Specialty Chemicals Corp. and bis(2,4,6-trimethylbenzoyl)-phenylposphineoxide (available, for example, under the trade designation "IRGACURE 819" from Ciba Specialty Chemicals Corp.).

Liquid or solvent in the gel can be exchanged with a second liquid, for example, by soaking the gel in the second liquid for a time sufficient to allow an exchange to occur. For example, water present in a gel can be removed by soaking the gel in a dry solvent (e.g., dry ethanol).

Aerogels described herein are formed by removing solvent from zirconia gels described herein without excessive shrinkage (e.g., not greater than about 10%). The gel structure should be strong enough to withstand at least some shrinkage and cracking during the drying (solvent removal).

The aerogels can be prepared by drying gels via super critical extraction. In some embodiments, the aerogels are prepared by drying gels under supercritical conditions of the solvent used in preparing the gel.

In some embodiments, of aerogels described herein, the crystalline metal oxide particles have an average primary particle size in a range from 2 nm to 50 nm (in some embodiments, 5 nm to 50 nm, 2 nm to 25 nm, 5 nm to 25 nm, 2 nm to 15 nm, or even 5 nm to 15 nm).

Typically, aerogels described herein have an organic content that is at least 3 (in some embodiments, at least 4, 5, 10, 15, or even at least 20) percent by weight, based on the total weight of the aerogel. In some embodiments, aerogels described herein have an organic content in a range from 3 to 30, 10 to 30, or even 10 to 20 percent by weight, based on the total weight of the aerogel.

Optionally, aerogels described herein comprise at least one of $Y_2O_3$ (e.g., in a range from 1 to 15, 1 to 9, 1 to 5, 6 to 9, 3.5 to 4.5, or even 7 to 8) mole percent of the crystalline metal oxide is $Y_2O_3$), $La_2O_3$ (e.g., up to 5 mole percent $La_2O_3$), $Al_2O_3$ (e.g., up to 0.5 mole percent $Al_2O_3$). One exemplary aerogel comprises in a range from 1 to 5 mole percent of the crystalline metal oxide is $Y_2O_3$, and in a range from 0 to 2 mole percent of the crystalline metal oxide is $La_2O_3$, and in a range from 93 to 99 mole percent of the crystalline metal oxide is $ZrO_2$. Another exemplary aerogel comprises in a range from 6 to 9 mole percent of the crystalline metal oxide is $Y_2O_3$, and in a range from 0 to 2 mole percent of the crystalline metal oxide is $La_2O_3$, and in a range from 89 to 94 mole percent of the crystalline metal oxide is $ZrO_2$. In another exemplary aerogel the crystalline metal oxide comprises in a range from 3.5 to 4.5 mole percent $Y_2O_3$, and in a range from 0 to 2 mole percent of the crystalline metal oxide is $La_2O_3$, and in a range from 93.5 to 96.5 mole percent $ZrO_2$. In another exemplary aerogel the crystalline metal oxide comprises in a range from 7 to 8 mole percent $Y_2O_3$, and in a range from 0 to 2 mole percent of the crystalline metal oxide is $La_2O_3$, and in a range from 90 to 93 mole percent $ZrO_2$. Other optional oxides that may be present in aerogels described herein include at least one of $CeO_2$, $Pr_2O_3$, $Nd_2O_3$, $Pm_2O_3$, $Sm_2O_3$, $Eu_2O_3$, $Gd_2O_3$, $Tb_2O_3$, $Dy_2O_3$, $Ho_2O_3$, $Er_2O_3$, $Tm_2O_3$, $Yb_2O_3$, $Fe_2O_3$, $MnO_2$, $Co_2O_3$, $Cr_2O_3$, $NiO$, $CuO$, $Bi_2O_3$, $Ga_2O_3$, or $Lu_2O_3$. Additives that may add desired coloring to the resulting crack free crystalline metal oxide articles include at least one of $Fe_2O_3$, $MnO_2$, $Co_2O_3$, $Cr_2O_3$, $NiO$, $CuO$, $Bi_2O_3$, $Ga_2O_3$, $Er_2O_3$, $Pr_2O_3$, $Eu_2O_3$, $Dy_2O_3$, $Sm_2O_3$, or $CeO_2$. In some embodiments, the amount of optional oxide(s) is in an amount in a range from about 10 ppm to 20,000 ppm. In some embodiments, it is desirable to have sufficient oxides present to so the crack free crystalline metal oxide articles has coloring of a tooth.

Aerogels described herein typically have a volume percent of oxide in a range of 3 to 20 (in some embodiments, 3 to 15, 3 to 14, or even 8 to 14) percent. Aerogels with lower volume percents of oxide tend to be very fragile and crack during supercritical drying or subsequent processing. Aerogels with higher oxide contents tend to crack during organic burnout because it is more difficult for volatile by-products to escape from the denser structure.

In some embodiments, aerogels described herein have a surface area in the range of 100 m2/g to 300 m2/g (in some embodiments, 150 m2/g to 250 m2/g), and a continuous pore channel size in a range of 10 nm to 20 nm. In some embodiments, the structure of, aerogels described herein is a composite of oxide particles, 3 nm to 10 nm (in some embodiments, 4 nm to 8 nm) in size and organics composed of acetate groups and polymerized monomers. The amount of organic is typically 10 to 20 weight percent of the aerogel.

Aerogels described herein can be made, for example, by providing a first zirconia sol comprising crystalline metal oxide particles having an average primary particle size of up to 50 nm (in some embodiments, 2 nm to 50 nm, 5 nm to 25 nm, 2 nm to 15 nm, or even 5 nm to 15 nm), wherein at least 70 (in some embodiments, at least 75, 80, 85, 90, 95, 96, 97, 98, or even at least 99; in a range from 70 to 99, 75 to 99, 80 to 99, or even 85 to 99) mole percent of the crystalline metal oxide is $ZrO_2$. The first zirconia sol is then optionally concentrated to provide a concentrated zirconia sol. A co-solvent, surface modifiers and optional monomers are added while stirring to obtain a well dispersed sol, wherein the cosolvent is optional).

A radical initiator (e.g., ultraviolet (UV) or thermal initiator) is added to the radically polymerizable surface-modified zirconia sol. Optionally the resulting sol is purged with $N_2$ gas to remove oxygen. The resulting sol is then gelled by radiating with actinic or heating at at least one temperature for a time sufficient to polymerize the radically surface-modified zirconia sol comprising the radical initiator to form a gel. Typically the resulting gel is a strong, translucent gel. The water, if present, is then removed from the gel via alcohol exchange to provide an at least partially de-watered gel. The gel is then converted to an aerogel by removing the alcohol, if present, from the partially de-watered gel via super critical extraction to provide the aerogel.

In one exemplary embodiment, removing the first liquid solvent from the at least partially de-watered gel comprises replacing the first liquid solvent with a second liquid solvent, then slowly increasing the temperature and pressure of the at least partially de-watered gels until supercritical conditions for the second solvent are obtained, then slowly releasing the pressure to about 1 bar to provide the monolithic aerogel.

In some embodiments, the complete exchange of the first liquid solvent with the second solvent is carried out under supercritical conditions. In some embodiments, the first liquid solvent is miscible with the second solvent. This method comprises placing the at least partially de-watered gel into a pressure vessel with a sufficient volume of the first liquid solvent to completely immerse the gel, pumping the second solvent into the autoclave at a temperature above the critical temperature of the second solvent until a pressure greater than the critical pressure of the second solvent is reached, maintaining the supercritical pressure in the pressure vessel for a time sufficient to complete the solvent exchange by pumping an additional quantity of the second solvent into the pressure vessel while simultaneously venting the mixture of the first and second solvents to a separator vessel, then slowly releasing the pressure to 1 bar to provide the monolithic aerogel. Typically, the second solvent is carbon dioxide.

Porous pre-sintered zirconia materials can have x, y, and z dimensions of at least 5 mm (in some embodiments, at least 10 mm, 15 mm, 20 mm, or even at least 25 mm) and a density of at least 30 (in some embodiments, at least 35, 40, 50, 95; in a range from 30 to 95) percent of theoretical density, and an average connected pore size in a range from 10 nm to 100 nm (in some embodiments, from 10 nm to 60 nm, 10 nm to 50 nm, 10 nm to 40 nm, or even from 10 nm to 30 nm), wherein at least 70 (in some embodiments, at least 75, 80, 85, 90, 95, 96, 97, 98, or even at least 99; in a range from 70 to 99, 75 to 99, 80 to 99, or even 85 to 99) mole percent of the metal oxide is crystalline $ZrO2$, and wherein the crystalline $ZrO2$ has an average grain size less than 100 nm (in some embodiments, in a range from 20 nm to 100 nm, 30 nm to 100 nm, or even 30 nm to 70 nm).

Optionally, the porous pre-sintered zirconia materials described herein comprise at least one of $Y2O3$ (e.g., in a range from 1 to 15, 1 to 5, 6 to 9, 3.5 to 4.5 or even 7 to 8 mol %), $La2O3$ (e.g., up to 5 mol %), $Al2O3$ (e.g., up to 0.5 mol %).

One exemplary porous pre-sintered zirconia material comprises in a range from 1 to 5 mol % $Y2O3$, and in a range from 0 to 2 mol % $La2O3$, and in a range from 93 to 99 mol % $ZrO2$.

Another exemplary porous pre-sintered zirconia material comprises in a range from 6 to 9 mol % $Y2O3$, and in a range from 0 to 2 mol % $La2O3$, and in a range from 89 to 94 mol % $ZrO2$.

Another exemplary porous pre-sintered zirconia material comprises in a range from 3.5 to 4.5 mol % $Y2O3$, and in a range from 0 to 2 mol % $La2O3$, and in a range from 93.3 to 96.5 mol % $ZrO2$.

Another exemplary porous pre-sintered zirconia material comprises in a range from 7 to 8 mol % $Y2O3$, and in a range from 0 to 2 mol % $La2O3$, and in a range from 90 to 93 mol % $ZrO2$.

In some embodiments, the porous pre-sintered zirconia material has a sulfate equivalent less than 5 ppm and/or a chloride equivalent less than 5 ppm. The raw material used to prepare the zirconia sol often contains chloride and sulfate impurities. Several thousand ppm by weight of these ions can be present in the calcined metal oxide article. If not removed these impurities can volatilize at the temperatures used for sintering and become entrapped in the sintered body as pores. The chloride and sulfate impurities can be removed prior to sintering, for example, by infiltrating the pre-sintered body with a solution of ammonia in water, allowing it to stand overnight and then exchanging the ammonia solution with water several times. During this treatment ammonia reacts with the chloride and sulfate impurities to form soluble ammonia salts. These are removed by diffusion into the water. It is also possible to remove these impurities by adjusting the heating profile so that sufficient volatilization occurs in the thermal treatment used to form the pre-sintered or calcined article.

Porous pre-sintered zirconia materials described herein can be made by a method comprising heating an aerogel described herein for a time and at at least one temperature sufficient to provide the porous pre-sintered zirconia material.

Typically, the aerogel is slowly heated at rates in the range from 5° C./h to 20° C./h to 600° C. to remove organics. Slow heating below 600° C. is typically necessary to volatize the organics without cracking the body, for example, because of nonuniform shrinkage or internal pressure of the volatile products. Thermogravimetric analysis and dilatometry can be used to track the weight loss and shrinkage which occurs at different heating rates. The heating rates in different temperature ranges can then be adjusted to maintain a slow and near constant rate of weight loss and shrinkage until the organics are removed. Careful control of the organic removal is critical to obtain crack-free bodies. Once the organic is removed the temperature can be raised at a faster rate (e.g., 100° C./h to 600° C./h) to a temperature in the range from 800° C. to 1100° C. and held at that temperature up to 5 h. At these temperatures the strength of the material increases by additional sintering, but an open pore structure is retained. When an ion-exchange treatment is used to remove chloride and sulfate impurities, the temperature and time used for heating the calcined body is such that it is strong enough to resist the capillary forces associated with infiltration of an ammonia solution. Typically this requires a relative density above 40% of theoretical (preferably above 45%). For articles that are to be milled, having the temperature too high and/or time too long can make milling difficult. In some cases it may be convenient to conduct the organic burnout separately; however, in that case care may be necessary to prevent absorption of moisture from the atmosphere prior to the higher temperature treatment. The aerogel can be quite fragile after heating to just 600° C., and non-uniform absorption of moisture can result in cracking.

The process of producing the zirconia ceramic dental article comprises the steps of a) providing the dental mill blank comprising the porous zirconia ceramic material, b) placing the dental mill blank in a machining device, c) machining the porous zirconia ceramic material to obtain a machined porous zirconia ceramic dental article.

The machining step is typically being done with or using a milling or grinding device. Those devices are commercially available e.g. from 3M ESPE (LAVA™ Form) or Sirona (CEREC™ inLab CAD/CAM).

Useful milling parameters include:
rotary speed of milling tool: 5,000 to 40,000 revisions/min;
feed rate: 20 to 5,000 mm/min;
milling cutter diameter: 0.8 to 4 mm.

The process of producing the zirconia ceramic dental article may further comprise the step of sintering the article obtained by machining the porous zirconia ceramic dental mill blank.

Sintering will result in a zirconia ceramic dental article, sometime also referred to as crystalline metal oxide article.

If conducted, the firing or sintering step should be accomplished under conditions which results in a dental ceramic article having an acceptable tooth like colour (e.g. a colour which fits into the Vita™ shade guide.

Useful sintering conditions can be characterized by one or more of the following parameters:
 temperature: from about 900 to about 1500° C. or from about 1000 to about 1400° C. or from about 1100° C. to about 1350° C. or from about 1200° C. to about 1400° C. or from about 1300° C. to about 1400° C. or from about 1320° C. to about 1400° C. or from about 1340° C. to about 1350° C.
 atmosphere: air or inert gas (e.g. nitrogen, argon);
 duration: until a density of about 95 or about 98 or about 99 to about 100% of the final density of the material has been reached.
 dwell time: from about 1 to about 24 h or from about 2 to about 12 h;
 pressure: ambient pressure.

A furnace which can be used is the commercially available Lava™ Therm (3M ESPE).

During the firing process the porous dental ceramic article is sintered to its final shape, thereby undergoing changes with regard to dimension, density, hardness, bending strength and/or grain size.

The dwell time (that is the time during which the article is kept at that temperature) is not really critical. The dwell time can be zero. The dwell time, however, can also be in a range from about 0 to about 24 h or from about 0.1 to about 5 h.

The firing temperature and dwell time (that is, the time period during which a particular temperature is kept) are typically correlated. A higher temperature typically requires only a short dwell time. Thus, the dwell time, may last from about 0 (e.g. if the firing temperature is about 1550° C.) to about 10 h (e.g. if the firing temperature is about 1100° C.) or from about 0.1 to about 8 h.

Generally, the sintering or firing conditions are adjusted such that the sintered dental ceramic article has a density of equal or greater than about 98% compared with the theoretically achievable density.

The zirconia ceramic dental article described herein may have an x, y, and z dimensions of at least 3 mm (in some embodiments, at least 5 mm, 10 mm, 15 mm, 20 mm, or even 25 mm) and a density of at least 98.5 (in some embodiments, 99, 99.5, 99.9, or even at least 99.99) percent of theoretical density, wherein at least 70 mole percent of the crystalline metal oxide is $ZrO_2$, and wherein the $ZrO_2$ has an average grain size less than 400 nanometers (in some embodiments, less than 300 nanometers, 200 nanometers, 150 nanometers, 100 nanometers, or even less than 80 nanometers).

Optionally, the zirconia ceramic dental article described herein may comprise at least one of $Y_2O_3$ (e.g., in a range from 1 to 15, 1 to 5, 6 to 9, 3.5 to 4.5 or even 7 to 8) mole percent of the crystalline metal oxide is $Y_2O_3$), $La_2O_3$ (e.g., up to 5 mole percent $La_2O_3$), $Al_2O_3$ (e.g., up to 0.5 mole percent $Al_2O_3$).

One exemplary zirconia ceramic dental article comprises in a range from 1 to 5 mole percent of the crystalline metal oxide is $Y_2O_3$, 0 to 2 mole percent of the crystalline metal oxide is $La_2O_3$ and in a range from 93 to 97 mole percent of the crystalline metal oxide is $ZrO_2$. This general composition has been observed to yield a combination of high biaxial flexure strength and good optical transmittance.

Another exemplary zirconia ceramic dental article comprises in a range from 6 to 9 mol % $Y_2O_3$, 0 to 2 mol % $La_2O_3$, and in a range from 89 to 94 mol % $ZrO_2$. This general composition range has been observed to yield a combination of good biaxial flexure strength and high optical transmittance.

Another exemplary zirconia ceramic dental article comprises in a range from 3.5 to 4.5 mol % $Y_2O_3$, 0 to 2 mol % $La_2O_3$, and in a range from 93.5 to 96.5 mol % $ZrO_2$. This general composition has been observed to yield a combination of especially high biaxial flexure strength and good optical transmittance.

Another exemplary zirconia ceramic dental article comprises in a range from 7 to 8 mol % $Y_2O_3$, 0 to 2 mol % $La_2O_3$, and in a range from 90 to 93 mol % $ZrO_2$. This general composition range has been observed a combination of good biaxial flexure strength and especially high optical transmittance.

The lower yttria compositions are believed to be more desirable where high strength is required and moderate optical transmittance is sufficient. The higher yttria compositions are believed to be more desirable where high optical transmittance is required and moderate strength is sufficient.

In another aspect, the present disclosure provides a method of making a zirconia ceramic dental article, the method comprising heating a calcined metal oxide article described herein for a time and at least one temperature sufficient to provide the crystalline metal oxide article.

Typically, the heating is conducted at at least one temperature in a range from 900° C. to 1500° C. (in some embodiments, from 1000° C. to 1400° C., 1000° C. to 1350° C., or even 1200° C. to 1300° C.). Typically, all the heating at or above 1000° C. is conducted in less than 24 hours; typically in a range from about 2 to about 24 hours. Typically, all the heating at or above 1000° C. is conducted at less than 1.25 atm. of pressure. Typically, the heating rate to temperature is in a range from 50° C./h. to 600° C./h. Heating can be conducted in conventional furnaces, preferably those with programmable heating capabilities. The material to be heated can be placed, for example, in an alumina crucible.

In some embodiments of the zirconia ceramic dental article, the $ZrO_2$ is all cubic $ZrO_2$. In some embodiments, the $ZrO_2$ is all tetragonal. In some embodiments, the zirconia is a mixture of tetragonal and cubic. Although not wanting to be bound by theory, based on the equilibrium phase diagram for $ZrO_2$ and $Y_2O_3$, mixtures of the cubic and tetragonal phases would be expected when the $Y_2O_3$ content is in the range from 2 to 8 mole percent and the material is sintered in the range from about 1200° C. to about 1250° C.

Embodiments with about 3.5 to 4.5 mol % $Y_2O_3$ with a mixture of tetragonal and some cubic structure exhibit an exceptional combination of strength and optical transmittance. The average grain size in one instance was 156 nm. When these materials are held at the sintering temperature for a prolonged time the grain size increased to 168 nm and the good transmittance of the material was substantially reduced. In a similar manner, if the sintering temperature was raised to about 1500° C. and held for 2 h, the grain size increased to 444 nm and the good optical transmittance was lost. It appears that maintaining the grain size of this composition below 175 nm is helpful for good optical transmission.

Embodiments containing about 7 to 8 mol % Y2O3, with a mixture of cubic and some tetragonal structure, exhibit the best transmittance, and may be particularly useful in applications where lower strength can be tolerated. This is surprising as it would be expected that compositions composed entirely of the cubic phase would exhibit the best transmission as there would be no tetragonal phase to scatter light.

The invention is also directed to the dental article obtainable or obtained by the process described in the present text.

The dental ceramic article may have the shape of a crown, bridge, inlay, onlay, veneer, facing, coping, crown and bridged framework, implant, abutment, orthodontic appliances (e.g. brackets, buccal tubes, cleats and buttons) and parts thereof and parts thereof.

The heat treatment for obtaining a sintered zirconia ceramic article is typically done under the following conditions:
temperature: from about 900° C. to about 1500° C. or from about 1000° C. to about 1400° C. or from about 1100° C. to about 1350° C. or from about 1200° C. to about 1400° C. or from about 1300° C. to about 1400° C. or from about 1320° C. to about 1400° C. or from about 1340° C. to about 1350° C.;
atmosphere: air or inert gas (e.g. nitrogen, argon);
pressure: ambient pressure;
duration: until a density of about 95 to about 100% of the final density of the material has been reached.

The dwell time (that is the time during which the article is kept at that temperature) is not really critical. The dwell time can be zero. The dwell time, however, can also be in a range from about 0 to about 24 h or from about 0.1 to about 5 h.

The ceramic dental article after a sintering step can usually be characterized by at least one or more of the following features:
density: fully sintered density of at least about 98.5 (in some embodiments, 99, 99.5, 99.9, or even at least 99.99) percent of theoretical density
Vickers hardness: from about 450 MPa to about 2200 MPa, or from about 500 MPa to about 1800 MPa. HV(2);
Phase content tetragonal phase: from about 1 to about 100 wt.-% or from about 10 to about 100 wt.-%; cubic phase: from about 30 to about 100 wt.-% or from about 50 to about 90 wt.-%;
Biaxial flexural strength: from about 450 MPa to about 2200 MPa, or from about 500 MPa to about 2000 MPa.

The dental article described in the present text does typically not contain components or additives which jeopardize the intended purpose to be achieved with the invention. Thus, components or additives added in an amount which finally results in a non-tooth-coloured dental article are usually not contained in the dental article. Typically, an article is characterized as not being tooth coloured if it cannot be allocated a colour from the Vita™ colour code system, known to the person skilled in the art. Additionally, components which will reduce the mechanical strength of the dental restoration to a degree, where mechanical failure will occur, are usually also not included in the dental article.

The zirconia ceramic dental article does usually not contain glass, glass ceramic materials, lithium disilicate ceramic materials, or combinations thereof.

The producing of the zirconia material described in the present text does typically also not require the application of a hot isostatic pressing step (HIP).

The complete disclosures of the patents, patent documents, and publications cited herein are incorporated by reference in their entirety as if each were individually incorporated.

EXAMPLES

The following examples are given to illustrate the invention described in the present text.

Unless otherwise indicated, all parts and percentages are on a weight basis, all water is deionized water, and all molecular weights are weight average molecular weight. Moreover, unless otherwise indicated all Experiments were conducted at ambient conditions (23° C.; 1013 mbar).

Materials Used for Producing Dental Mill Blanks

TABLE 1

| Material name or abbreviation | Description |
| --- | --- |
| MEEAA | 2-(2-(2-Methoxyethoxy) Ethoxy) Acetic Acid obtained from Aldrich Chemical Company, Milwaukee, WI |
| Zirconium acetate | An aqueous solution of zirconium acetate containing nominally 16.3 weight percent Zr obtained from Magnesium Elektron, Inc., Flemington, NJ. The aqueous solution was exposed to an ion exchange resin (obtained under the trade designation "AMBERLYTE IR 120" from Rohm and Haas Company, Philadelphia, PA) before use (oxide content 21.85 wt. %) |
| DI water | De-ionized water |
| Yttrium acetate | Yttrium (III) acetate tetrahydrate obtained from AMR Technologies Inc., Toronto, Canada (oxide content 33.4 wt. %) |
| 1-Methoxy-2-propanol | An alcohol obtained from Aldrich Chemical Company |
| 2-Hydroxyethyl methacrylate (HEMA) | An acrylate monomer obtained from Aldrich Chemical Company |
| Triethylamine | A base obtained from Aldrich Chemical Company |
| Lanthanum Acetate | Lathanum (III) acetate hydrate obtained from Alfa Aesar, Ward Hill, MA (oxide content 45.5 wt. %) |
| Acrylamide | Acrylamide obtained from Alfa Aesar |
| 1-vinyl-2-pyrrolidione | 1-vinyl-2-pyrrolidione obtained from Alfa Aesar |

TABLE 1-continued

| Material name or abbreviation | Description |
|---|---|
| 2,2'-Azobis(2-methylbutyronitrile), ("VAZO 67") | 2,2'-Azobis(2-methylbutyronitrile), obtained from E. I. du Pont de Nemours and Company, Wilmington, DE under the trade designation "VAZO 67" |
| Ethoxylated Pentaerythritol Tetraacrylate ("SR454") | Ethoxylated Pentaerythritol Tetraacrylate, obtained from Sartomer Company Inc., Exton, PA, under the trade designation "SR454" |
| Ethoxylated Pentaerythritol Tetraacrylate ("SR494") | Ethoxylated Pentaerythritol Tetraacrylate, obtained from Sartomer Company Inc., under the trade designation "SR494" |
| Polyethylene Glycol (400) dimethacrylate ("SR603") | Polyethylene Glycol (400) dimethacrylate, obtained from Sartomer Company Inc., under the trade designation "SR603" |
| Ethoxylated (9) Trimethylolpropane Triacrylate ("SR502") | Ethoxylated (9) Trimethylolpropane Triacrylate Obtained from Sartomer Company Inc., under the trade designation "SR502" |
| Ethoxylated (15) Trimethylolpropane Triacrylate ("SR9035") | Ethoxylated (15) Trimethylolpropane Triacrylate Obtained from Sartomer Company Inc., under the trade designation "SR9035" |
| Butyl Acrylate | Butyl Acrylate obtained from Alfa Aesar |
| Tosoh TZ-3YSB-E | Yttrium stabilized zirconia powder; lot# 309682, lot# 461889 |

Preparation of a $ZrO_2$ (88 Mol %)/$Y_2O_3$ (12 Mol %) Sol

A useful description how to produce a sol is given below. All sols were prepared accordingly by varying the content of components used. Sol compositions are reported in mole percent inorganic oxide.

The hydrothermal reactor was prepared from 15 meters of stainless steel braided smooth tube hose (0.64 cm inside diameter, 0.17 cm thick wall; obtained under the trade designation "DUPONT T62 CHEMFLUOR PTFE" from Saint-Gobain Performance Plastics, Beaverton, Mich.). This tube was immersed in a bath of peanut oil heated to the desired temperature. Following the reactor tube, a coil of an additional 3 meters of stainless steel braided smooth tube hose ("DUPONT T62 CHEMFLUOR PTFE"; 0.64 cm I.D., 0.17 cm thick wall) plus 3 meters of 0.64 cm stainless-steel tubing with a diameter of 0.64 cm and wall thickness of 0.089 cm that was immersed in an ice-water bath to cool the material and a backpressure regulator valve was used to maintain an exit pressure of 2.76 MPa.

A precursor solution was prepared by combining the zirconium acetate solution (2.000 grams) with DI water (2205.3 grams). Yttrium acetate (327.8 grams) was added while mixing until full dissolution. The solids content of the resulting solutions was measured gravimetrically (120° C./hr. forced air oven) to be 22.16 wt.-%. D.I. water (718 grams) was added to adjust the final concentration to 19 wt.-%. This procedure was repeated three times to give a total of about 15.115 grams of precursor material. The resulting solution was pumped at a rate of 11.48 ml/min. through the hydrothermal reactor. The temperature was 225° C. and the average residence time was 42 minutes. A clear and stable zirconia sol was obtained.

Table 2 is a summary of the compositions and the process conditions used for other sols produced in a similar manner to Sol C1.

TABLE 2

| Sol | $ZrO_2$ [mol %] | $Y_2O_3$ [mol %] | $La_2O_3$ [mol %] | Residence time [min] | Temperature, [° C.] |
|---|---|---|---|---|---|
| T1 | 95.7 | 2.3 | 2 | 42 | 225 |
| T2 | 97.7 | 2.3 | 0 | 42 | 207 |
| C1 | 88 | 12 | 0 | 42 | 225 |
| C2 | 88 | 12 | 0 | 42 | 207 |

Sol Concentration and Diafiltration

The resulting sols were concentrated (20-35 wt. % solids) first via ultrafiltration using a membrane cartridge (obtained under the trade designation "M21S-100-01P" from Spectrum Laboratories Inc., Rancho Dominguez, Calif.), and then via constant volume diafiltration using the same membrane cartridge. The resulting sol was then further concentrated via rotary evaporation.

Gel Preparation

The gels were prepared by combining the sols to obtain the desired oxide composition and adjusting the oxide, acetic acid and solvent composition via diafiltration, distillation or a combination thereof. The acrylic acid, hema and initiator were added, the sol placed in a mold and thermally cured at 50 C for 4 hr. A typical procedure is given for one gel of Example G1 below. The composition of the all the gels are given Table 3 (the solvent is made up of water and ethanol).

Example G1

A 90.46 g sample of Sol C1 (prepared and diafiltered and concentrated as described above, 35.34 wt. % oxide and 4.14 wt. % acetic acid) and 256.82 g of Sol T1 (prepared and diafiltered and concentrated as described above, 33.46 wt. % oxide and 2.78 wt. % acetic acid) were charged in to a 1000 ml RB flask. Water (169.38 g) was removed via rotary evaporation resulting in viscous somewhat dry material. Ethanol (82.68 g), acrylic acid (11.52 g), HEMA (5.90 g) were added to the flask. The contents were stirred overnight resulting is a fluid translucent sol. 2,2'-azobis(2-methylbutyronitrile) ("VAZO 67") (0.601 g) was added and stirred until dissolved. The contents of the flask were then purged with $N_2$ gas for 6 min. The sample (translucent and low viscosity) was charged to cylindrical containers (29 mm diameter). Each container was about 18 ml in volume and each was sealed on both ends (very little air gap was left between the top and liquid). The samples were allowed to stand for about 1 h then placed in an oven to cure (50° C., 4 h). This resulted in a clear translucent blue gel. The gel was removed from the container and placed in a 473 ml wide mouth jar (three gels per jar). The jar was filled with ethanol (275 g, denatured). The sample was soaked for 24 h then the ethanol was replaced with fresh ethanol. The sample was soaked for 24 h then the ethanol was replaced with a third batch of fresh ethanol. The sample was allowed to soak until the supercritical extraction was done. The above manipulations were done minimizing the amount of time the gel was exposed to the air.

Table 3 is a summary of the gel production conditions used for other gels produced in a similar manner to Example G1.

TABLE 3

| Ex. | T-sol:C-sol | T-sol:C-sol (wt %) | Oxide (wt %) | Acetic acid (wt %) | Acrylic acid (wt %) | Hema (wt %) | Solvent |
|---|---|---|---|---|---|---|---|
| G1 | T1:C1 | 75.5:24.5 | 39.32 | 3.43 | 4.15 | 2.12 | 50.98 |
| G2 | T2:C2 | 75.5:24.5 | 39.33 | 3.82 | 4.14 | 2.12 | 50.59 |
| G3 | T2:C2 | 75.5:24.5 | 39.96 | 5.9 | 4.24 | 2.17 | 47.73 |
| G4 | T2 | 100:0 | 40.3 | 5.76 | 4.24 | 2.17 | 47.53 |

Extraction Process

The gels were loaded into the supercritical extractor. The wet $ZrO_2$-based gels were removed separately from the ethanol bath, weighed, placed individually inside small canvas pouches, and then stored briefly in another ethanol bath before being loaded into the 10-L extractor vessel. For extraction of the Example G1 gels, about 3500 ml of 200-proof ethanol was added to the 10-L extractor of a laboratory-scale supercritical fluid extractor unit. The canvas bags containing the wet zirconia-based gels were transferred from the ethanol bath into the 10-L extractor so that the wet gels were completely immersed in the liquid ethanol inside the jacketed extractor vessel, which was heated and maintained at 60° C. After the extractor vessel lid was sealed in place, liquid carbon dioxide was pumped by a chilled piston pump (setpoint: −12.5° C.) through a heat exchanger to heat the CO2 to 60° C. and into the 10-L extractor vessel until an internal pressure of 11.0 MPa was reached. At these conditions, carbon dioxide is supercritical. Once the extractor operating conditions of 11 MPa and 60° C. were met, a PID-controlled needle valve regulated the pressure inside the extractor vessel by opening and closing to allow the extractor effluent to pass through a porous 316L stainless steel frit (obtained from Mott Corporation as Model #1100S-5.480 DIA-.062-10-A), then through a heat exchanger to cool the effluent to 30° C., and finally into a 5-L cyclone separator vessel that was maintained at room temperature and pressure less than 5.5 MPa, where the extracted ethanol and gas-phase CO2 were separated and collected throughout the extraction cycle for recycling and reuse. Supercritical carbon dioxide (scCO2) was pumped continuously through the 10-L extractor vessel for 7 hours from the time the operating conditions were achieved. After the 7-hour extraction cycle, the extractor vessel was slowly vented into the cyclone separator over 16 hours from 11 MPa to atmospheric pressure at 60° C. before the lid was opened and the dried canvas pouches containing the aerogel were removed.

The dry aerogels were removed from their canvas pouches and transferred into 237 ml glass jars packed with tissue paper for storage.

The dry aerogels were semi-translucent with a bluish tint.

Burnout/De-Binder Process

The extracted aerogel samples from Example G1 from above were removed from their closed container and set on an aluminium oxide plate, covered with aluminium oxide cylinders and fired in air according to the following schedule in a chamber furnace ("Nabertherm 60 liter"): i—heat from 20° C. to 220° C. at 18° C./h rate; ii—heat from 220° C. to 244° C. at 1° C./h rate; iii—heat from 244° C. to 400° C. at 6° C./h rate; iv—heat from 400° C. to 900° C. at 60° C./h rate; v—hold at 900° C. for 2 h and vi—cool down from 900° C. to 20° C. at 600° C./h rate.

After burnout process, the samples were crack free. All aerogels from Example G2-G4 were de-bindered in a similar manner as described for Example G1.

Pre-sintering Process

The de-bindered samples of Example G1-G4 were set on an aluminium oxide plate and fired in air according to the following schedule in a chamber furnace (Nabertherm 1 liter): i—heat from 20° C. to 900° C. at 10° C./min. rate; ii—heat from 900° C. to Tx ° C. at 2° C./min. iii—hold at Tx for y hours and iv—cool down from Tx to 600° C. in 1 h. Pre-sintering steps were finished when furnace was cooled down to room temperature. The different temperatures Tx and dwell times y are shown in Table 5.

Measurements

Method for Measuring N2 Sorption Isotherms, BET Surface Area, Pore Volume, Average Connected Pore Diameter The samples were run on either on a QUANTACHROME AUTOSORB-1 BET Analyzer" (Quantachrome Instruments, Boynton Beach, Fla.) or a BELSORP-mini instrument (BEL Japan Inc., Osaka, Japan). The samples were weighed and outgassed at 200° C. for two days then subjected to a $N_2$ sorption process with an appropriate number and distribution of measurement points, e.g. 55 adsorb points and 20 desorb points from a $p/p_0$ range $1 \times 10^6$ to 1 and back to 0.05 giving full isotherms. The specific surface area S was calculated by the BET method (Details regarding calculation see Autosorb-1 Operating Manual Ver. 1.51 IV. Theory and Discussion; Quantachrome Instruments, Inc.). The total pore volume $V_{liq}$ is derived from the amount of vapor adsorbed at a relative pressure close to unity ($p/p_0$ closest to 1), by assuming that the pores are then filled with liquid adsorbate (Details regarding calculation see Autosorb-1 Operating Manual Ver. 1.51 IV. Theory and Discussion; Quantachrome Instruments, Inc.). The average pore diameter (d) is calculated from the surface area (S) and the total pore volume ($V_{liq}$):

$$d = \frac{4Vliq}{S}$$

Average Grain Size

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Particle Size

Particle size measurements were made using a light scattering particle sizer equipped with a red laser having a 633 nm wavelength of light (obtained under the trade designation "ZETA SIZER—Nano Series, Model ZEN3600" from Malvern Instruments Inc., Westborough, Mass.). Each sample was analyzed in a one centimeter square polystyrene sample cuvette. The sample cuvette was filled with about 1 gram of deionized water, and then a few drops (about 0.1 gram) of the zirconia-based sol were added. The composition (e.g., sample) within each sample cuvette was mixed by drawing the composition into a clean pipette and discharging the composition back into the sample cuvette several times. The sample cuvette was then placed in the instrument and equilibrated at 25° C. The instrument parameters were set as follows: dispersant refractive index 1.330, dispersant viscosity 1.0019 MPa-second, material refractive index 2.10, and material absorption value 0.10 units. The automatic size-measurement procedure was then run. The instrument automatically adjusted the laser-beam position and attenuator setting to obtain the best measurement of particle size.

The light scattering particle sizer illuminated the sample with a laser and analyzed the intensity fluctuations of the light scattered from the particles at an angle of 173 degrees. The method of Photon Correlation Spectroscopy (PCS) was used by the instrument to calculate the particle size. PCS uses the fluctuating light intensity to measure Brownian motion of the particles in the liquid. The particle size is then calculated to be the diameter of sphere that moves at the measured speed.

The intensity of the light scattered by the particle is proportional to the sixth power of the particle diameter. The Z-average size or cumulant mean is a mean calculated from the intensity distribution and the calculation is based on assumptions that the particles are mono-modal, mono-disperse, and spherical. Related functions calculated from the fluctuating light intensity are the Intensity Distribution and its mean. The mean of the Intensity Distribution is calculated based on the assumption that the particles are spherical. Both the Z-average size and the Intensity Distribution mean are more sensitive to larger particles than smaller ones.

The Volume Distribution gives the percentage of the total volume of particles corresponding to particles in a given size range. The volume-average size is the size of a particle that corresponds to the mean of the Volume Distribution. Since the volume of a particle is proportional to the third power of the diameter, this distribution is less sensitive to larger particles than the Z-average size. Thus, the volume-average will typically be a smaller value than the Z-average size.

Density

If desired, the density of the pre-sintered or sintered material can be measured by an Archimedes technique. The measurements is made on a precision balance (identified as "AE 160" from Mettler Instrument Corp., Hightstown, N.J.) using a density determination kit (identified as "ME 33360" from Mettler Instrument Corp.).

To measure the density of the pre-sintered material the sample is first weighed in air (A). Then the sample is immersed in water using vacuum overnight. The immersed sample is weighed in air (B) and then weighed under water (C). The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho=(A/(B-C))\,\rho 0$, where $\rho 0$ is the density of water.

To measure the density of the sintered material the sample is first weighed in air (A), then immersed in water (B) The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho=(A/(A-B))\,\rho 0$, where $\rho 0$ is the density of water.

The relative density can be calculated by reference to the theoretical density ($\rho t$) of the material, $\rho rel=(\rho/\rho t)100$.

Vickers Hardness

If desired, the Vickers hardness can be determined according to ISO 843-4 with the following modifications: The surface of the samples are ground using silicon carbide grinding paper (P400 and P1200). The test forces are adjusted to the hardness level of samples. Used test forces were between 0.2 kg and 2 kg and were applied for 15 s each indentation. A minimum of 10 indentations is measured to determine the average Vickers hardness. The tests can be conducted with a hardness tester Leco M-400-G (Leco Instrumente GmbH).

Biaxial Flexural Strength

If desired, the biaxial flexural strength can be determined according to ISO 6872 (2008) with the following modifications: The sample is sawn into wafers with a thickness of 1 to 2 mm using a dry or wet cut saw The diameter of the samples should be between 12 and 20 mm. Each wafer is centred on a support of three steel balls. The support diameter depends on the sample diameter and should have maximum 14 mm and should be at least 1 mm smaller than the sample diameter. The punch diameter in contact with the wafer is 3.6 mm. The punch is pushed onto the wafer at a rate of 0.1 mm per min. A minimum of 6 samples is measured to determine the average strength. The tests can be conducted in an Instron 5566 universal testing machine (Instron Deutschland GmbH).

Testing

A Machinability

The millability of the dental mill blanks was determined as follows:

Mill blocks showing different hardness were produced by variating the heat treatment conditions according the pre-sintering procedure above (e.g. variation of temperature between 900° C. and 1090° C. and dwell time between 0 and 2 hs).

For conducting the milling tests, the pre-sintered mill blocks were glued in the middle of a suitable milling frame. The mill blanks were placed in a Lava™ milling device (Lava™ CNC 500, 3M Deutschland GmbH; 3M ESPE). The mill blanks were milled to obtain a machined dental article. In some examples the standard milling parameters of the Lava™ CNC 500 were used. In some other examples the rotary speed of milling tool and the feed rate were reduced to a rate of 45% of standard parameters. As dental articles anterior or molar copings or monolithic molars were milled.

For conducting the grinding tests, the pre-sintered mill blanks were glued on Cerec™ sample holders and placed in a Cerec™ Milling device (inlab MCXL, Sirona GmbH; Bensheim-Germany). A monolithic molar tooth was designed with a Cerec™ Software (3.8, inlab 3D). The tooth was milled out of the block with standardized milling parameter (ParadigmC™ milling parameter, bur left: cylinder step bur 12, bur right: cylinder pointed bur 12).

The machinability of the mill blanks was assessed by dental technicians. The break of a milling tool or a bad milling quality of the milled dental articles resulted in the assessment "no millability".

For comparison, dental mill blanks produced by compacting a zirconia powder from Tosoh Comp. were also analysed.

For this purpose a ready-to-press powder Type TZ-3Y SB-E (Tosoh Company; Japan) were compacted in an axial compacting press to the targeted density of 3.2-3.15 g/cm³. Afterwards a binder burn-out were performed at a $T_{max}$=450° C. The pre-sintering-step was performed with a heating rate of 100 K/h up to the wanted temperatures and shown dwell times listed in Table 5. The block dimensions after pre-sintering were approximately 19.2 by 18.9 by 23.9 mm.

TABLE 4

| Sample | Powder batch |
|---|---|
| L1 | Tosoh TZ3YSB-E #309682 |
| L2 | Tosoh TZ3YSB-E #461889 |

Results:

The Vickers hardness, biaxial flexure strength, and results as regards millability are shown in Table 5 and FIG. 1.

It was found that the dental mill blanks described in the present text can be machined at higher Vickers hardness and lower strength compared to Lava™ Frame Multi material (3M ESPE) and dental mill blanks produced by compacting commercially available zirconia powder.

A first set of experiments for grinding dental restorations using the material described in the present text showed excellent results as well.

In FIG. 1 the dependency of hardness and biaxial flexural strength of the porous dental ceramic material described in the present text and a porous dental ceramic material according to the state of the art is shown.

TABLE 5

| Material/Sample | T (dwell) [° C.] | Biaxial flexural strength [MPa] | Vickers hardness (HV load) | millable yes/no |
|---|---|---|---|---|
| G1 | 900 (2 h) | 3.3 | 6.8 (HV 0.2) | Yes |
| G1 | 950 (0 h) | 3.9 | 10.4 (HV 0.5) | Yes |
| G1 | 950 (2 h) | 8.1 | 18.8 (HV 0.5) | Yes |
| G1 | 1000 (0 h) | 5.6 | 17.9 (HV 0.5) | Yes |
| G1 | 1000 (2 h) | 9.6 | 40.1 (HV 1) | Not milled |
| G1 | 1050 (0 h) | 11.5 | 46.0 (HV 1) | Yes |
| G1 | 1050 (2 h) | 30.4 | 147.3 (HV 1) | Not milled |
| G1 | 1090 (0 h) | 21.8 | 122.1 (HV 2) | Yes |
| G2 | 975 (2 h) | n.m. | 21.5 (HV 1) | Yes |
| G2 | 1000 (2 h) | n.m. | 39.7 (HV 1) | Yes |
| G2 | 1025 (2 h) | n.m. | 76.6 (HV 1) | Yes |
| G2 | 1050 (2 h) | n.m | 150.4 (HV 1) | No; break of milling tool |
| L1 | 840 (4 h) | 9.9 | 17 (HV 0.5) | Yes |
| L1 | 880 (4 h) | 14.8 | 19 (HV 0.5) | Not milled |
| L1 | 920 (4 h) | 23.6 | 23 (HV 0.5) | Not milled |
| L1 | 960 (4 h) | 28.9 | 29 (HV 0.5) | Not milled |
| L1 | 1000 (4 h) | 38.7 | 35 (HV 0.5) | Not milled |
| L1 | 1040 (4 h) | 50.2 | 44 (HV 0.5) | Yes |
| L1 | 1080 (4 h) | 82.5 | 60 (HV 0.5) | Yes |
| L2 | 1100 (4 h) | 69.7 | 78 (HV 0.5) | Yes |
| L2 | 1120 (4 h) | 72.3 | 81 (HV 0.5) | Yes |
| L2 | 1140 (4 h) | 114.0 | 126 (HV 0.5) | No; break of milling tool |
| L2 | 1100 (4 h) | 69.7 | 78 (HV 0.5) | Yes |
| L2 | 1120 (4 h) | 72.3 | 81 (HV 0.5) | Yes |
| L2 | 1140 (4 h) | 114.0 | 126 (HV 0.5) | Yes | n.m.: not measured (due to a lack of test samples)

B Milling Dust Analysis

A way to visualize the milling dust adherence is to sonicate milled parts (e.g. crowns) in water.

An inventive and a comparative dental mill blank (commercially available Lava™ Plus mill block; 3M Deutschland GmbH; 3M ESPE Dental Division) were milled on a Lava™ CNC 500 milling machine operated with the Lava™ Design 7.2 software package to obtain crowns. As inventive sample mill blanks from example G2 pre-sintered at 1020° C. with 2 hours dwell time were used.

Milling dust produced during milling the inventive and the comparative mill block on a Lava™ CNC 500 machine was collected after the milling of crowns (as described above).

The volume related particle size distribution was analyzed using a particle size analyser (CILAS 1064, Fa. Quantacrome GmbH&Co KG.). The dusts were measured in wet mode under water The solid particles were dispersed by sonication (60 sec). The volume related particle size distribution was analyzed between 0.04 and 500 μm, divided into 100 sections. The results are shown in a density distribution q3. The results and differences of a Lava™ Plus mill block (fine curve) compared to the inventive block (bold curve) are shown in FIG. 2.

It is shown that the volume of particles smaller than 1 μm is more within the dust collected when milling a Lava™ Plus material than within the dust collected when milling the inventive material. The volume of particles smaller than 1 μm of the Lava™ Plus material is about 28.5%, in contradiction to the inventive material, where the particle volume smaller than 1 μm is only about 6.3%.

If desired, the differences of dust adhesion of dust obtained when machining the material of the inventive mill block and the comparative mill block can also be visualized as follows:

The machined article is submersed in 20 ml de-mineralized water in a 50 ml glass beaker and sonicated in an ultrasonic bath at room temperature for 20 sec. (Sonorex RK100H device, Bandelin comp.). The resulting turbidity of the water can be used as a direct measure for the quantity of the adhered dust.

The crowns described above yielded the following results: material of the inventive mill block: essentially clear water (see photo on the right hand side of FIG. 3); material of the comparative mill block: essentially turbid suspension (see photo on the left hand side of FIG. 3).

C Adaptation of Shape of Crown Using Manual Grinding and Milling Tools

As inventive sample mill blanks from example G2 pre-sintered at 1020° C. with 2 hours dwell time were used. As comparative material Lava™ Plus 20 mm mill blank (3M ESPE) was used.

Figure 4:
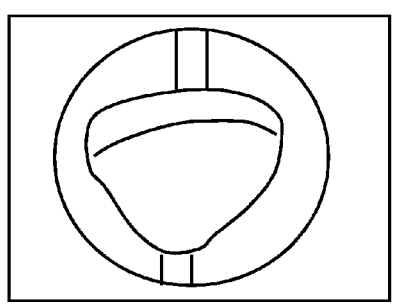
FIG. 4 schematically shows a frame with a milled dental restoration (anterior, full contour crown) contained therein.
Figure 5:
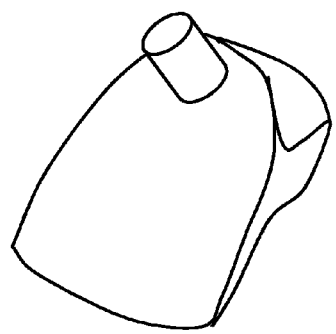
FIG. 5 schematically shows an intermediate milled dental restoration (anterior, full contour crown) obtained when removing it from the frame.
Figure 6:
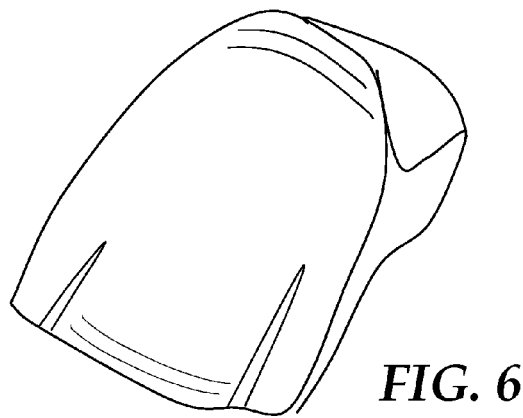
FIG. 6 schematically shows a milled dental restoration (anterior, full contour crown) with individual modifications at the incisal edge and cervical area.

The milled dental restorations (anterior, full contour crown, see FIG. 4), were removed from the respective mill block by carefully cutting the connecting sprues with a cross cut carbide bur ("Figure198-Cut40, Horico comp.) fixed in hand piece ("K4", KaVo comp.)" at 20,000 rpm (i) resulting in intermediate milled crowns (see FIG. 5). The rest of the sprues remaining on the surface of the crown subsequently was flattened and smoothened with the same tool at the same speed of rotation (ii). The same tool and speed of rotation was used in order to adjust the fine features of the contour like individual features at the incisal edge and cervical area (iii) yielding a crown with desired final highly defined shape (see FIG. 6).

When carrying out the manual adaptation process steps (i) to (iii) the material of the inventive mill block was easy to handle and to tune to the desired shape and surface features of the restoration.

The material of the inventive mill blanks showed a similarity in consistence to carveable steatite (Soapstone) during the manual rework, whereas the material of the comparative mill block exhibited a more chalky consistency.

Manually shaping the surface of the dental restoration obtained from the comparative mill block with a tool was more difficult compared to the shaping of the material of the inventive mill block. E.g., it was more difficult to adjust the manually applied forces to get the desired features in a reproducible manner.

So, even for inexperienced dental lab technicians it was easier to get highly defined surfaces of dental restorations when using the material of the inventive mill blanks than when using material of the state of the art.

The improved adaptability of the material of the inventive mill blanks can also be demonstrated by a reduced depth of grooves/notches when it is notched under standardized conditions. In order to quantify the differences the following experiment was conducted.

As comparative material Lava™ Plus 20 mm mill blank (3M ESPE) was used.

The mill blocks from Example G4 were pre-sintered at 1025° C. for 2 hours according the pre-sintering procedure above. The mill blocks were sawn into disks with a diameter of 17 mm and a height of 1.7 mm. A notch was created using a razor blade (Martor Type no. 37/0.1 mm) which was running 15 s on the surface of the samples without additional weight. The used apparatus was a notching device (EXAKT Apparatebau GmbH, Type 6010, Serial no. 0012), the applied notching speed was stage 1 of the device speed scale.

To measure the notch depth and the radius of the notch ground a Laser Scanning Microscope (Keyence VK9710) was used. The VK-9710 scans the field of the microscope using a laser beam and an X-Y scan optical system. The light receiving element detects reflecting light from each pixel in the field of view. Driving the objective lens in the Z-axis and scanning repeatedly obtains reflecting light intensity based on the Z position. Height information is obtained and reflecting light intensity is detected while focusing on the peak position. Each pixel on a single plane (1024×768 pixels) obtains data for the reflecting light intensity (Intensity) based on the Z position. The reflecting light intensity at the Z position and its color information are obtained and combined to 3D-data.

The scanning of the samples was conducted with the following parameters: 50× optical magnification, quality "superfine", mode "surface profile" and a z-stage of 0.5 μm. Measurement lines were aligned perpendicular to the notch. The measurement lines represent the profile of the notch.

The notch depth was measured by marking two points which indicates the surface level of the sample and deepest level of the notch on the notch profile (sector method). The notch ground radius was determined by fitting a circle on the above mentioned notch profile (3-point method). Notch depth and radius of the notch ground were determined three times for every sample. The measurements were repeated three times at different locations of the notch. The results are given in Table 6.

TABLE 6

| Material | Notch depth [μm] | Notch ground radius [μm] |
| --- | --- | --- |
| G4 | 85.602 +/− 0.763 | 2.234 +/− 0.155 |
| Lava™ Plus (lot #466760) | 100.338 +/− 0.399 | 3.666 +/− 0.248 |

What is claimed is:

1. A dental mill blank comprising a porous pre-sintered zirconia material, comprising:
   the porous pre-sintered zirconia material showing a $N_2$ adsorption and/or desorption of isotherm type IV according to IUPAC classification;
   the porous pre-sintered zirconia material having a Vickers hardness from about 25 to about 150; and
   an attachment for reversibly attaching the dental mill blank to a machining device.

2. The dental mill blank of claim 1, the porous pre-sintered zirconia material being characterized by at least one of the following features:
   showing a nitrogen adsorption and desorption isotherm with hysteresis loop;
   showing a hysteresis loop of type H1 according to IUPAC classification;
   showing a $N_2$ adsorption and desorption isotherm with a hysteresis loop in a $p/p_0$ range of 0.70 to 0.95;
   average connected pore diameter: from about 10 to about 100 nm;
   average grain size: less than about 100 nm;
   BET surface: from about 10 to about 200 $m^2/g$;
   Biaxial flexural strength: from about 10 MPa to about 40 MPa;
   x, y, z dimension: at least about 5 mm;
   Vickers hardness: from about 35 to about 140;
   density: about 30 to about 95% of theoretical density;
   having an isotropic shrinkage behaviour.

3. The dental mill blank according to claim 2, the porous pre-sintered zirconia material being further characterized by at least one of the following features:
   $ZrO_2$ content: from about 70 to about 98 mol %;
   $HfO_2$ content: from about 0 to about 2 mol %;
   $Y_2O_3$ content: from about 1 to about 15 mol %;
   $Al_2O_3$ content: from about 0 to about 1 mol %.

4. The dental mill blank according to claim 1 having the shape of a disc or block.

5. The dental mill blank according to claim 1, the attachment for reversibly attaching the dental mill blank to a machining device being selected from frame(s), stump(s) and combinations thereof.

6. The dental article according to claim 1, the attachment for reversibly attaching the dental mill blank to a machining device being selected from groove(s), notch(es), recess(es), stamp(s), and combinations thereof.

7. The dental mill blank according to claim 1, the porous pre-sintered zirconia material being obtained by a process comprising the step of heat treating an aerogel.

8. The dental mill blank according to claim 7, the aerogel being characterized by at least one of the following features:
- comprising crystalline zirconia particles having an average primary particle diameter in a range from about 2 nm to about 50 nm;
- content of crystalline zirconia particles: at least about 85 mol.-%;
- having a surface area in the range of 100 $m^2/g$ to 300 $m^2/g$;
- having an organic content of at least about 3 wt.-%.

9. The dental mill blank according to claim 7, the aerogel having been heat treated to a temperature of about 900 to about 1100° C.

10. The dental mill blank according to claim 1, the porous pre-sintered zirconia material being obtained by a process comprising the steps of
- providing a zirconia sol comprising crystalline metal oxide particles,
- optionally concentrating the first zirconia sol to provide a concentrated zirconia sol,
- adding a radically reactive surface modifier to the zirconia sol to provide surface-modified particles of the zirconia sol and adding a radical initiator to the radically polymerizable surface-modified particles of the zirconia sol,
- casting the zirconia sol into a mold to provide a casted zirconia sol,
- curing the radically polymerizable surface-modified particles of the zirconia sol to form a gel,
- optionally removing water, if present, from the gel via a solvent exchange to provide an at least partially dewatered, solvent containing gel,
- extracting solvent, if present, from the gel by super critical extraction to provide an aerogel,
- optionally cutting the aerogel into smaller pieces,
- heat treating the aerogel.

11. A process of producing a zirconia dental article comprising the steps of:
- providing a dental mill blank comprising a porous pre-sintered zirconia material comprising:
  - the porous pre-sintered zirconia material showing a $N_2$ adsorption and/or desorption of isotherm type IV according to IUPAC classification;
  - the porous pre-sintered zirconia material having a Vickers hardness from about 25 to about 150; and
  - an attachment for reversibly attaching it to a machining device;
- placing the dental mill blank in a machining device; and
- machining the porous zirconia material.

12. The process according to claim 11, the machining step being done with a milling, drilling, cutting, carving, or grinding device.

13. The process according to claim 11 comprising the additional step of sintering the machined porous zirconia material.

14. A dental article obtained by the process described in claim 11.

15. The dental article of claim 14 having the shape of a crown, bridge, inlay, onlay, veneer, facing, coping, crown and bridged framework, implant, abutment, orthodontic appliances and parts thereof.

* * * * *

UNITED STATES PATENT AND TRADEMARK OFFICE
CERTIFICATE OF CORRECTION

PATENT NO. : 9,592,105 B2
APPLICATION NO. : 14/418973
DATED : March 14, 2017
INVENTOR(S) : Hauptmann It is certified that error appears in the above-identified patent and that said Letters Patent is hereby corrected as shown below:

On the Title Page

Item [56], Column 2
Line 2, delete "ZrO2" and insert -- ZrO2 --, therefor.

In the Specification

Column 1
Line 43, delete "for" and insert -- tor --, therefor.

Column 5
Line 5, delete "substractive" and insert -- subtractive --, therefor.

Column 7
Line 52, delete "wear wear" and insert -- wear --, therefor.

Column 14
Lines 4-5, delete "autogeneous" and insert -- autogenous --, therefor.

Column 20
Line 28, delete "pthalic" and insert -- phthalic --, therefor.

Column 20
Lines 30-31, delete "hydoxypropyl" and insert -- hydroxypropyl --, therefor.

Column 20
Line 31, delete "hydoxypropyl" and insert -- hydroxypropyl --, therefor.

Column 21
Line 3, delete "azobisisobututyronitrile" and insert -- azobisisobutyronitrile --, therefor.

Signed and Sealed this
Thirty-first Day of October, 2017

Joseph Matal
*Performing the Functions and Duties of the
Under Secretary of Commerce for Intellectual Property and
Director of the United States Patent and Trademark Office*

Column 21
Lines 8-9, delete "(cyclohexanecabonitrile)" and insert -- (cyclohexanecarbonitrile) --, therefor.

Column 21
Line 21, delete "4-(2-hydroxyethoxyl)" and insert -- 4-(2-hydroxyethoxy) --, therefor.

Column 21
Line 27, delete "phenylposphineoxide" and insert -- phenylphosphineoxide --, therefor.

Columns 27-28
Line 52, delete ""AMBERLYTE" and insert -- "AMBERLITE --, therefor.

Column 29
Line 63, delete "$Y_2O_3$" and insert -- $Y_2O_3$ --, therefor.

Column 30
Line 29, delete "$Y_2O_3$" and insert -- $Y_2O_3$ --, therefor.

Column 36
Lines 30-31, delete "Quantacrome GmbH&Co" and insert -- Quantachrome GmbH & Co --, therefor.

In the Claims

Column 38
Line 64, Claim 6, delete "stamp(s)," and insert -- stump(s), --, therefor.